US009255930B2

(12) United States Patent
Pemberton et al.

(10) Patent No.: US 9,255,930 B2
(45) Date of Patent: Feb. 9, 2016

(54) BNP-SP ANTIBODIES

(71) Applicant: OTAGO INNOVATION LIMITED, North Dunedin (NZ)

(72) Inventors: Christopher Joseph Pemberton, Christchurch (NZ); Arthur Mark Richards, Christchurch (NZ); Michael Gary Nicholls, Christchurch (NZ); Timothy Grant Yandle, Christchurch (NZ)

(73) Assignee: OTAGO INNOVATION LIMITED (NZ)

( * ) Notice: Subject to any disclaimer, the term of this patent is extended or adjusted under 35 U.S.C. 154(b) by 0 days.

(21) Appl. No.: 13/863,343

(22) Filed: Apr. 15, 2013

(65) Prior Publication Data

US 2013/0316378 A1    Nov. 28, 2013

Related U.S. Application Data

(60) Division of application No. 13/439,841, filed on Apr. 4, 2012, which is a continuation of application No. 12/381,100, filed on Mar. 6, 2009, now Pat. No. 8,298,772, which is a continuation of application No. PCT/NZ2007/000265, filed on Sep. 7, 2007.

(60) Provisional application No. 60/842,649, filed on Sep. 7, 2006.

(51) Int. Cl.
| | |
|---|---|
| *C07K 16/00* | (2006.01) |
| *C07K 16/18* | (2006.01) |
| *C07K 16/44* | (2006.01) |
| *G01N 33/68* | (2006.01) |
| *C07K 14/58* | (2006.01) |
| *C07K 16/26* | (2006.01) |
| *G01N 33/74* | (2006.01) |

(52) U.S. Cl.
CPC ............ *G01N 33/6887* (2013.01); *C07K 14/58* (2013.01); *C07K 16/26* (2013.01); *G01N 33/6893* (2013.01); *G01N 33/74* (2013.01); *G01N 2800/32* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,196,265 A | 4/1980 | Koprowski et al. |
| 4,816,567 A | 3/1989 | Cabilly et al. |
| 5,221,685 A | 6/1993 | Obata et al. |
| 5,310,687 A | 5/1994 | Bard et al. |
| 5,334,708 A | 8/1994 | Chang et al. |
| 5,480,792 A | 1/1996 | Buechler et al. |
| 5,504,013 A | 4/1996 | Senior |
| 5,525,524 A | 6/1996 | Buechler et al. |
| 5,571,698 A | 11/1996 | Ladner et al. |
| 5,631,171 A | 5/1997 | Sandstrom et al. |
| 5,647,124 A | 7/1997 | Chan et al. |
| 5,679,526 A | 10/1997 | Buechler et al. |
| 5,719,060 A | 2/1998 | Hutchens et al. |
| 5,719,600 A | 2/1998 | Alcorn |
| 5,744,305 A | 4/1998 | Fodor et al. |
| 5,792,294 A | 8/1998 | Randazzo et al. |
| 5,821,047 A | 10/1998 | Garrard et al. |
| 5,824,799 A | 10/1998 | Buechler et al. |
| 5,843,708 A | 12/1998 | Hardman et al. |
| 5,851,776 A | 12/1998 | Valkirs |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,020,153 A | 2/2000 | Hardman et al. |
| 6,057,098 A | 5/2000 | Buechler et al. |
| 6,107,623 A | 8/2000 | Bateman et al. |
| 6,113,855 A | 9/2000 | Buechler |
| 6,124,137 A | 9/2000 | Hutchens et al. |
| 6,143,576 A | 11/2000 | Buechler |
| 6,204,500 B1 | 3/2001 | Whitehouse et al. |
| 6,225,047 B1 | 5/2001 | Hutchens et al. |
| 6,235,241 B1 | 5/2001 | Catt et al. |
| 6,268,144 B1 | 7/2001 | Koster |
| 6,329,209 B1 | 12/2001 | Wagner et al. |
| 6,399,398 B1 | 6/2002 | Cunningham et al. |
| 6,780,645 B2 | 8/2004 | Hayter et al. |
| 7,045,366 B2 | 5/2006 | Huang et al. |

(Continued)

FOREIGN PATENT DOCUMENTS

| | | |
|---|---|---|
| WO | 2005/003154 A2 | 1/2005 |
| WO | 2005/052593 A1 | 6/2005 |
| WO | 2006/007667 A1 | 1/2006 |
| WO | 2006/131529 A1 | 12/2006 |
| WO | 2009/004315 A1 | 1/2009 |

OTHER PUBLICATIONS

Riechmann et al., Nature, 1988, 323-327, 332(6162).
Sambrook et al. (Eds.), Molecular Cloning, A Laboratory Manual, 2nd Ed., 1989, Cold Spring Harbor Press (Table of Contents).
Skyler, Diabetes Care, 1984, 118-129, Suppl. 1.
Solberg, J. Clin. Chem. Clin. Biochem., 1987, 645-656, 25.

(Continued)

*Primary Examiner* — Elizabeth C Kemmerer
(74) *Attorney, Agent, or Firm* — Acuity Law Group, P.C.; Bradford J. Duft; Daniel M. Chambers

(57) ABSTRACT

The invention provides methods for predicting, diagnosing or monitoring acute cardiac disorders, cardiac transplant rejection, or distinguishing acute cardiac disorders from pulmonary disorders, by measuring BNP signal peptide levels in a sample taken from a subject shortly after onset of, or presentation with the disorder or transplant rejection.

22 Claims, 8 Drawing Sheets

(56) References Cited

U.S. PATENT DOCUMENTS

| | | | |
|---|---|---|---|
| 7,057,165 B2 | 6/2006 | Koopman et al. |
| 7,476,724 B2 | 1/2009 | Dennis et al. |
| 8,298,772 B2 | 10/2012 | Pemberton et al. |
| 8,507,209 B2 | 8/2013 | Pemberton et al. |
| 2003/0054494 A1 | 3/2003 | DeSauvage et al. |
| 2003/0083251 A1 | 5/2003 | Westenfelder |
| 2004/0157293 A1 | 8/2004 | Evans et al. |
| 2005/0064511 A1 | 3/2005 | Buechler et al. |
| 2005/0244902 A1 | 11/2005 | Gotze et al. |
| 2005/0244904 A1 | 11/2005 | Ng |
| 2006/0234315 A1 | 10/2006 | MacFadyen et al. |
| 2008/0312179 A1 | 12/2008 | Pecker |

OTHER PUBLICATIONS

Squire et al., Clin. Sci. (Lond.), 2004,309-316, 107(3).
Stewart (Ed.), Solid-Phase Peptide Synthesis, 1969, WH Freeman Co., San Francisco, CA (Table of Contents).
Suresh et al., Methods Enzymol., 1986, 210-228, 121.
Tapanainen et al., J. Am. Coll. Cardiol., 2004, 757-763, 43(5).
Tatusov et al., Science, 1997, 631-637, 278(5338).
Thibault et al., Peptides, 1988, 47-53, 9(1).
Thomas, Proc. Natl., Acad. Sci. USA, 1980, 5201-5205, 77(9).
Thompson et al., Nucleic Acids Res., 1994, 4673-4680, 22(22).
Trigilia et al., Nucleic Acids Res., 1998, 8186, 16(16).
Troughton et al., J. Am. Coll. Cardiol., 2004, 416-422, 43(3).
Troughton et al., Lancet 2000, 1126-1130, 355(9210).
Vaughn et al., Nat. Biotechnol., 1998, 535-539, 16(6).
Verhoeyen et al., Science, 1988, 1534-1536, 239(4847).
Wheeler et al., Nucleic Acids Res., 2001, 11-16, 29(1).
Wild (Ed.), The Immunoassay Handbook, 3rd Ed., 2005, 103, 121-126, Elsevier Ltd.
Zola (Ed.), Monoclonal Antibodies: A Manual of Techniques, 1987, 147-158, CRC Press, Inc 1987.
Agrawal (Ed.), Protocols for Oligonucleotides and Analogs, Synthesis and Properties, 1993, vol. 20, Humana Press Inc., NJ (Table of Contents).
Atherton et al. (Eds.), Solid Phase Synthesis: a practical approach, 1989, IRL Oxford Press, Oxford, England (Table of Contents).
Bartlett, Decline in Microbial Studies for Patients with Pulmonary Infections, Clin. Infect. Dis., 2004, 170-172, 39(2).
Centers for Disease Control and Prevention, Pneumonia FastStats Sheet, Jan. 2012.
Chang et al., Novel strategy for identification of candidate cytotoxic T-cell epitopes from human preproinsulin, Tissue Antigens, 2003, 408-417, 62(5).
Clackson et al., Making antibody fragments using phage display libraries, Nature, 1991, 624-628, 352(6336).
Coligan et al.(Eds.), Current Protocols in Immunology vol. 1, 1991, Wiley-Interscience, New York, NY, USA (Table of Contents Only).
Congia et al., T cell epitopes of insulin defined in HLA-DR4 transgenic mice are derived from preproinsulin and proinsulin, Proc. Natl. Acad. Sci. USA, 1998, 3833-3838, 95(7).
Cwirla et al., Peptides on phage: A vast library of peptides for identifying ligands, Proc. Natl. Acad. Sci. USA, 1990, 6378-6382, 87(16).
Dale et al. (Eds.), From Genes to Genomes: Concepts and Applications of DNA Technology, Ed. 2, 2007, Wiley, NY (Table of Contents).
Devlin et al., Random Peptide Libraries: A Source of Specific Protein Binding Molecules, Science, 1990, 404-406, 249(4967).
Ducimetiere et al., Relationship of Plasma Insulin Levels to the Incidence of Myocardial Infarction and Coronary Heart Disease Mortality in a Middle-aged Population, Diabetologia, 1980, 205-210, 19(3).
Evertsen et al., Diagnosis and management of pneumonia and bronchitis in outpatient primary care practices, Prim. Care Resp. J., 2010, 237-241, 19(3).
Fischer et al., A readers' guide to the interpretation of diagnostic test properties: clinical example of sepsis, Intensive Care Med., 2003, 1043-1051, 29(7).
Freshney (Ed.), Culture of Animal Cells, 2nd Ed., 1987, Alan R. Liss, Inc., NY (Table of Contents).
Gait (Ed.), Oligonucleotide Synthesis: A Practical Approach, 1984, IPL Press, Oxford, Washington DC (Table of Contents).
Garcia et al., Ghrelin and Cardiovascular health, Curr. Opin. Pharmacol., 2006, 142-147, 6(2).
Gennis et al., Clinical Criteria for the Detection of Pneumonia in Adults: Guidelines for Ordering Chest Roentgenograms in the Emergency Department, J. Emerrg. Med., 1989, 263-268, 7(3).
Gilchrist et al., Immunoneutralization of Growth Differentiation Factor 9 Reveals It Partially Accounts for Mouse Oocyte Mitogenic Activity, Biology and Reproduction, 2004, 732-739, 71(3).
Golemis (Ed.), Protein-protein Interactions: A Molecular Cloning Manual, 2002, Cold Springs Harbor, NY (Table of Contents).
Harlow et al. (Ed.), Using Antibodies: A Laboratory Manual, 1999, Cold Spring Harbor Publications, NY (Table of Contents).
Hermanson (Ed.), Bioconjugate Techniques, 1996, Academic Press, San Diego, CA (Table of Contents).
Hindiyeh et al., Evaluation of the Prodesse Hexaplex Multiplex PCR Assay for Direct Detection of Seven Respiratory Viruses in Clinical Specimens, Am. J. Clin. Pathol., 2001, 218-224, 116(2).
Hofmann, Gene Expression Profiling by Microarrays: Clinical Implications, 2006, Cambridge University Press (Table of Contents).
Holliger et al., "Diabodies": Small bivalent and bispecific antibody fragments, Proc. Natl. Acad. Sci. USA. 1993, 6444-6448, 90(14).
Howard et al. (Eds.), Making and Using Antibodies: A Practical Handbook, 2007, CRC Press (Table of Contents).
Klee, Interferences in hormone immunoassays, Clin. Lab. Med., 2004, 1-18, 24(1).
Lundblad (Ed.), Techniques in Protein Modification Edition: 2, 1995, CRC Press, (Table of Contents).
Mandell, Epidemiology and etiology of community-acquired pneumonia, Infect. Dis. Clin. North Am., 2004, 761-776, 18(4).
Miller et al. (Eds.), Gene Transfer Vectors for Mammalian Cells, 1987, Cold Springs Harbor, NY (Table of Contents).
Morrison et al., Chimeric human antibody molecules: Mouse antigen-binding domains with human constant region domains, Proc. Natl. Acad. Sci. USA, 1984, 6851-6855 81(21).
Muller et al. (Eds.), Microarray Technology and its Application, 2005, Springer (Table of Contents).
Munson et al., Ligand: A Versatile Computerized Approach for Characterization of Ligand-Binding Systems, Anal. Biochem., 1980, 220-239, 107(1).
Murdoch et al., Breathing New Life into Pneumonia Diagnostics, J. Clin. Micro., 2009, 3405-3408, 47(11).
Naghavi et al., From Vulnerable Plaque to Vulnerable Patient : A Call for New Definitions and Risk Assessment Strategies: Part I, Circulation, 2003, 1664-1672, 108(14).
Nelson et al., A computer program for calculating antibody affinity constants, Comput. Methods Programs Biomed., 1988, 65-68, 27(1).
Ng et al., Biomedical applications of protein chips, J. Cell. Mol. Med., 2002, 329-340, 6(3).
NIH Guide, Molecular and Physical Characterization of the Vulnerable Plaque, 1997, 26(37).
Paul (Ed.), Fundamental Immunology, 2nd ed., 1989, Raven Press, NY (Table of Contents).
Pluckthun, Antibodies in *Escherichia coli*, in Rosenburg et al. (Eds.), The Pharmacology of Monoclonal Antibodies, 1994, 113, 269-315, Ch. 11, Springer-Verlag.
Raju et al., T Cell Recognition of Human Pre-Proinsulin Peptides Depends on the Polymorphism at HLA DQ Locus: A Study Using HLA DQ8 and DQ6 Transgenic Mice, Hum. Immunol., 1997, 21-29, 58(1).
Ronco et al., Cardiorenal Syndrome, J. Am. Coll. Cardiol., 2008, 1527-1539, 52(19).
Schuetz et al., Procalcitonin and other biomarkers to improve assessment and antibiotic stewardship in infections—hope for hype?, Swiss Med. Wkly., 2009, 318-326, 139(23-24).
Scopes (Ed.), Protein Purification: Principles and Practice, 1987, Springer-Verlag, NY (Table of Contents).

(56) References Cited

OTHER PUBLICATIONS

Scott et al., Searching for Peptide Ligands with an Epitope Library, Science, 1990, 386-390, 249(4967).
Sharma et al., Radiological imaging in pneumonia: recent innovations, Curr. Opin. Pulm. Med., 2007, 159-169, 13(3).
Skowera et al., CTLs are targeted to kill beta cells in patients with type 1 diabetes through recognition of a glucose-regulated preproinsulin epitope, J. Clin. Invest., 2008, 3390-3402, 118(10).
Summah et al., Biomarkers: A Definite Plus in Pneumonia, Mediators Inflamm. 2009, 675753, 1-9.
Tatusova et al., Blast 2 Sequences, a new tool for comparing protein and nucleotide sequences, FEMS Microbiol Lett., 1999, 247-250, 174(2).
Thygesen et al., Universal definition of myocardial infarction, Circulation, 2007, 2634-2653, 116(22).
Toma et al., Recognition of Human Proinsulin Leader Sequence by Class I—Restricted T-Cells in HLA-A*0201 Transgenic Mice and in Human Type 1 Diabetes, Diabetes, 2009, 394-402, 58(2).
Van Erp et al., Application of a Sol Particle Immunoassay to the Dertimination of Affinity Constants of Monoclonal Antibodies, J. Immunoassay, 1991, 425-443, 12(3).
Viljoen et al., Molecular diagnostic PCR handbook, 2005, Springer (Table of Contents).
Waiker et al., Imperfect Gold Standards for Kidney Injury Biomarker Evaluation, J. Am. Soc. Nephrol., 2012, 13-21, 23(1).
Walker (Ed.), Protein Protocols Handbook, 2nd Ed., 2002, Humana Press, Totowa, NJ (Table of Contents).
Ward et al., Binding activities of a repertoire of single immunoglobulin variable domains secreted from *Escherichia Coli*, Nature, 1989, 544-546, 341(6242).
Weir (Ed.), Handbook of Experimental Immunology, 4th Ed., 1986, vol. 1, Blackwell Scientific Publications, Oxford (Table of Contents).
Werno et al., Laboratory diagnosis of invasive pneumococcal disease, Clin. Infect. Dis., 2008, 926-932, 46(6).
Wilson et al., Simplified conjugation chemistry for coupling peptides to F(ab') fragments: autologous red cell agglutination assay for HIV-1 antibodies, J. Immunol. Methods, 1994, 267-273, 175(2).
Yarmush et al., Coupling of antibody-binding fragments to solid-phase supports: site-directed binding of F(ab') 2 fragments, J. Biochem. Biophys. Methods, 1992, 285-297, 25(4).
Zapata et al., Engineering linear F(ab')2 fragments for efficient production in *Escherichia coli* and enhanced antiproliferative activity, Protein Eng., 1995, 1057-1062, 8(10).
Abbott Press Release, New Point of Care Test Helps Physicians Quickly, Accurately Assess Difficult-to-Diagnose Heart Failure at Patient's Bedside, Jul. 26, 2006, retrieved online Dec. 13, 2007at URL: http://www.abbott.com/global/url/pressRelease/en_US/60.5/Press_Release-0339.htm.
Altschul et al., Nucleic Acid Res., 1997, 3389-3402, 25(17).
Antman et al., in Braunwald et al. (Eds.), Heart disease: a textbook of cardiovascular medicine, 6th ed., 2001, 1114-1231, vol. 2, Ch. 35.
Apple et al., Circulation, 2007, e352-e355, 115(13).
Bairoch et al., Nucleic Acids Res., 1994, 3583-3589, 22(17).
Baxevanis, Nucleic Acids Res., 2001, 1-10, 29(1).
Bolton et al., Proc. Natl. Acad. Sci., 1962, 1390-1397, 48(8).
Bowie et al., Science, 1990, 1306-1310, 247(4948).
Braud et al., Nature, 1998, 795-799, 391(6669).
Brennan et al., Science, 1985, 81-83, 229(4708).
Chenna et al., Nucleic Acids Res., 2003, 3497-3500, 31(13).
Cohen, Proc. Natl. Acad. Sci. USA, 1972, 2110-2114, 69(8).
Deutscher (Ed.), Methods in Enzymology, 1990, 182 (Table of Contents).
Dieuguez et al., Eur. J. Endocrinol., 2000, 413-417, 142(5).
Falquet et al., Nucleic Acids Res., 2002, 235-238, 30(1).
Feng et al., J. Mol. Evol., 1987, 351-360, 25(4).
Frohman, Methods Enzymol., 1993, 340-356, 218.
Giesen et al., Nucleic Acids Res., 1998, 5004-5006, 26(21).
Gutierrez-Marcos et al., Eur. Heart J., 1991, 503-507, 12(4).
Harlow et al. (Eds.), Antibodies, A Laboratory Manual, 1988, 92-117, Ch. 5, Cold Spring Harbor Publications, NY.
Hess et al., Clin. Lab., 2005, 167-172, 51(3-4) (Abstract Only).
Hofmann et al., Nucleic Acids Res., 1999, 215-219, 27(1).
Hoogenboom et al., J. Mol. Biol., 1992, 381-388, 227(2).
Huang, Comput. Appl. Biosci., 1994, 227-235, 10(3).
Hunt et al., Clin. Endocrinol., 1997, 287-296, 47(3).
Huston et al., Proc. Natl. Acad. Sci. USA, 1988, 5879-5883, 85(16).
Jain, Med. Device Technol., 2004, 14-17, 15(4).
Jernberg et al., J. Am. Coll. Cardiol., 2002, 437-445, 40(3).
Jones et al., Nature, 1986, 522-525, 321(6069).
Jung et al., Nephrol. Dial. Transplant, 2004, 3117-3123, 19(12).
Kohler et al, Nature, 1975, 495-497, 256(5517).
Kunkel, Proc. Natl. Acad. Sci. USA, 1985, 488-492, 82(2).
Lutz et al., Exp. Cell. Res., 1988, 109-124, 175(1).
Matteucci et al., J. Am. Chem. Soc., 1981, 3185-3191, 103(11).
Mehra et al., Am. J. Cardiol. 2004, 454-458, (94(4), Pubmed Abstract PMID 15325298.
Merrifield, J. Am. Chem. Soc. 1963, 2149-2154, 85(14).
Milstein et al., Nature, 1983, 537-540, 305(5934).
Mullis et al. (Eds.), The Polymerase Chain Reaction, 1994, Birkhauser (Table of Contents).
Needleman et al., J. Mal. Biol., 1970, 443-453, 48.
Neuberger, Nat. Biotechnol., 1996, 826, 14(7).
Nielsen et al., Science, 1991, 1497-1500, 254(5037).
Notredame et al., J. Mol. Biol., 2002, 205-217, 302(1).
Omland et al., Circulation, 1996, 1963-1969, 93(11).
Omland et al., Circulation, 2002, 2913-2918, 106(23).
Pemberton et al., Hypertension, 2000, 355-359, 36(3).
Poykko et al., Diabetes, 2003, 2546-2553, 52(10).
Reyzer et al., J. Proteome Res., 2005, 1138-1142, 4(4).
Rice et al., Trends Genet., 2000, 276-277, 16(6).
Richards et al., Circulation, 1998, 1921-1929, 97(19).
Richards et al., J. Am. Coll. Cardiol., 2002, 1182-1188, 39(7).
Bennet et al., The risk of myocardial infarction is enhanced by a synergistic interaction between serum insulin and smoking, Eur. J. Endocrinol., 2002, 641-647, 147(5).
Lindahl et al., High Proinsulin Concentration Precedes Acute Myocardial Infarction in a Nondiabetic Population, Metabolism, 1999, 1197-1202, 48.
Martoglio et al., Signal sequences: more than just greasy peptides, Trends Cell. Biol., 1998, 410-415, 8(10).

Figure 1.

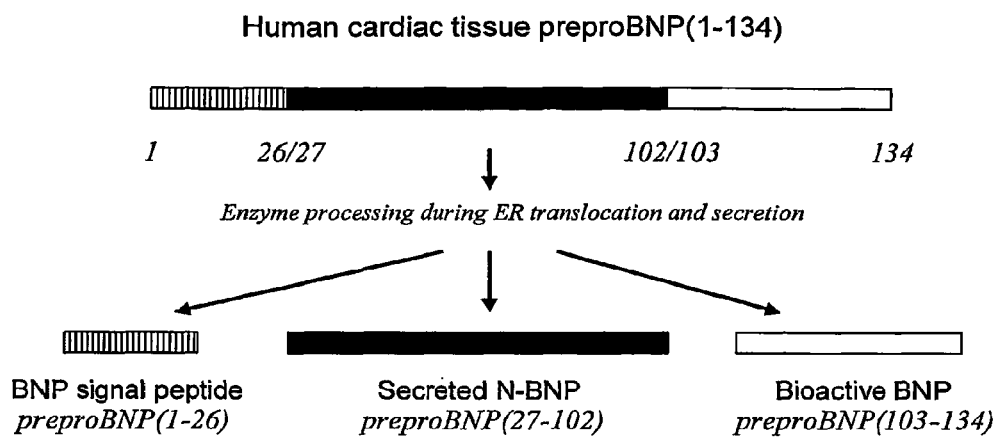

Human cardiac tissue preproBNP(1-134)

1      26/27      102/103      134

Enzyme processing during ER translocation and secretion

BNP signal peptide
*preproBNP(1-26)*

Secreted N-BNP
*preproBNP(27-102)*

Bioactive BNP
*preproBNP(103-134)*

Figure 2B.

| | |
|---|---|
| Human/1-26 | MDPQ*T*APS*R*ALLLLLFL*H*LAFLGG*R*S |
| Cat/1-26 | MDPKTALL*R*ALLLLLFL*H*LSPLGG*R*S |
| Sheep/1-26 | MDPQKAL*SR*TLLLLLFL*H*LSLLGC*R*S |
| Pig/1-25 | MGP*R*MALP*R*-VLLLLFL*H*LLLLGC*R*S |
| Dog/1-26 | MEPCAALP*R*ALLLLLFL*H*LSPLGG*R*P |
| Rat/1-26 | MDLQKVLPQMILLLLFL*N*LSPLGG*HS* |
| Mouse/1-26 | MDLLKVLSQMILFLLFL*Y*LSPLGG*HS* |
| | *    .    :   *.****    **   : . |

" * " means that the residues in that column are identical in all sequences in the alignment.
" . " means that conserved substitutions have been observed.
" : " means that semi-conserved substitutions are observed.

Residue sorting according to physiochemical criteria
| | | |
|---|---|---|
| AVFPMILW | normal text | small (small + hydrophobic (including aromatic-Y) |
| DE | black | Acidic |
| RHK | bold | Basic |
| STYHCNGQ | italics | Hydroxyl + Amine + Basic-Q |

Figure 2A.

Human  (Genbank accession No. NP_002512.1)
MDPQTAPSRALLLLLFLHLAFLGGRSHPLGSPGSASDLETSGLQEQRNHLQGKLSELQVEQTSLEPLQESPRPTGVWKSREVATEGIRGHRKMVLY
TLRAPRSPKMVQGSGCFGRKMDRISSSSGLGCKVLRRH Rat  (Genbank accession No. NP_113733)
MDLQKVLPQMILLLLFLNLSPLGGHSHPLGSPSQSPEQSTMQKLLELIREKSEEMAQRQLSKDQGPTKELLKRVLRSQDSAFRIQERLRNSKMAHS
SSCFGQKIDRIGAVSRLGCDGLRLF Sheep  (Genbank accession No. AAB92565)
MDPQKALSRTLLLLFLHLSLLGCRSHPLGGPGSASELPGLQELLDRLRDRVSELQAEQLRVEPLQQGQGLEETWDSPAAAPAGFLGPHHSLLQAL
RGPKMMRDSGCFGRRLDRIGSLSGLGCNVLRRY Pig  (Genbank accession No. NP_999011)
MGPRMALPRVILLLFLHLILLGCRSYPLGGAGLASELPGIQELLDRLRDRVSELQAERTDLEPLRQDRGLTEAWEAREAAPTGVLGPRSSIFQVLR
GIRSPKIMRDSGCFGRRLDRIGSLSGLGCNVLRRY Mouse  (Genbank accession No. NP_032752)
MDLLKVLSQMILFLLFLYLSPLGGHSYPLGSPSQSPEQFKMQKLLELIREKSEEMAQRQLLKDQGLTKEHPKRVLRSQGSTLRVQQRPQNSKVTHI
SSCFGHKIDRIGSVSRLGCNALKLL Dog  (Genbank accession No. P16859)
MEPCAALPRALLLLFLHLSPLGGRPHPLGGRSPASEASEASEASGLWAVQELLGRLKDAVSELQAEQLALEPLHRSHSPAEAPEAGGTPRGVLAP
HDSVLQALRLRSPKMHKSGCFGRRLDRIGSLSGLGCNVLRKY Cat  (Genbank accession No. AAG13661)
MDPKTALIRALLLLFLHLSPLGGRSHPLGGPPASEASAIQELLDGLRDTVSELQEAQMALGPLQQGHSPAESWEAQEEPPARVLAPHDNVLRAL
RRLGSSKMMRDSRCFGRRLDRIGSLSGLGCNVLRRH

Figure 8.

| Peptide | Cross reactivity with BNP-SP antiserum (%) |
|---|---|
| BNP-SP | 100 |
| proBNP(1-13) | <0.003 |
| proBNP(1-76) | <0.01 |
| proANP(1-30) | <0.009 |
| ANP | <0.008 |
| BNP | <0.009 |
| Endothelin 1 | <0.006 |
| Angiotensin II | <0.003 |
| Angiotensin(1-7) | <0.01 |
| Urotensin II | <0.003 |
| CNP | <0.006 |
| proCNP(1-15) | <0.008 |
| Adrenomedullin | <0.01 |
| Urocortin I | <0.01 |
| Urocortin II | <0.01 |

BNP-SP ANTIBODIES

RELATED APPLICATIONS

This application is a divisional of commonly owned, co-pending U.S. patent application Ser. No. 13/439,841, filed 4 Apr. 2012, which is a continuation application based on commonly owned U.S. application Ser. No. 12/381,100, filed 6 Mar. 2009 and issued on 30 Oct. 2012 as U.S. Pat. No. 8,298,772, which is a continuation application of commonly owned PCT application no. PCT/NZ2007/000265, filed on 7 Sep. 2007 and published on 13 Mar. 2008 as WIPO publication no. WO/2008/030122, which is based on commonly owned U.S. provisional patent application Ser. No. 60/842,649, filed on 7 Sep. 2006. This application claims the benefit of and priority to each of the foregoing patent applications for any and all purposes, and each of them is hereby incorporated by reference in its entirety.

FIELD OF THE INVENTION

This invention relates to BNP signal peptide (BNP-SP) and its use in the prognosis, diagnosis and monitoring of acute cardiac disorders including acute coronary syndromes in a subject resulting in release of biomarker into the circulation. More particularly, the invention relates to methods of predicting, diagnosing or monitoring an acute cardiac disorder in a subject by measuring BNP-SP levels in a sample taken shortly after onset of, or at clinical presentation with the disorder.

BACKGROUND

Acute cardiac disorders including acute coronary syndromes (ACS) encompass a wide spectrum of cardiac ischemic events ranging from unstable angina through to acute myocardial infarction (AMI). AMI presents as the most serious of these events and therefore requires rapid and accurate diagnosis. Patients who present with two or more of the described features (a history of ischemic chest discomfort, evolutionary changes on serial electrocardiogram (ECG) traces and a rise and fall in plasma cardiac biomarkers) are clearly identified as undergoing AMI.[1] However, a significant proportion of patients (40%-50%) who present with suspected AMI do not have serial changes on ECG, or typical symptoms thus placing heavy emphasis on circulating biomarker concentrations for accurate diagnosis.[2-4]

Accurate early diagnosis of myocardial infarction facilitates prompt introduction of reperfusion treatment, including effective percutaneous or thrombolytic revascularisation and adjunctive anticoagulant and anti-platelet therapy. Such treatments are progressively less effective at reducing mortality and morbidity with each hour of delay in diagnosis and management.[2-4] Given the need for accelerated decision-making in this clinical situation, there is considerable interest in the identification of circulating biomarkers providing an early and specific diagnosis of acute cardiac disorders, particularly AMI.

A number of biomarkers have been proposed for this purpose, including creatine kinase-MB (CK-MB), troponin T (TnT), troponin I (TnI) and myoglobin, but there are limitations to their use. Time to detectable or abnormal elevation of plasma cardiac biomarkers can be 6 hours (myoglobin, CK-MB) to 12 hours (TnT, TnI) with peak levels not occurring until 24-48 hours after onset of injury, imposing a window of delay upon precise diagnosis and treatment.[1-4] Furthermore, both myoglobin and CK-MB are non-specific and can be secreted from extra-cardiac cardiac sources, especially during trauma or surgery. Other biomarkers useful for this purpose are BNP (preproBNP 103-134) and N-BNP (preproBNP (27-134) which is also known as NT-proBNP (see FIG. 1). Both peptides are secreted into the circulation.

Measurement of plasma concentrations of BNP and N-BNP early post-AMI has powerful prognostic value[2,6,7] and incorporation of plasma concentrations of these peptides into treatment regimes can significantly improve clinical outcomes of patients with heart failure.[8] This is particularly true of N-BNP which has a half-life some 14-fold longer than BNP[5] and thus provides additional important information regarding long term cardiac performance after AMI.

As with the cardiac biomarkers above, BNP and N-BNP may not reach detectable or abnormal levels for 6 to 12 hours after onset of injury, with peak levels not occurring until 24 to 48 hours after onset. The long term diagnostic/predictive powers of BNP and N-BNP therefore lack the accompanying power of a specific marker providing early specific diagnosis of acute cardiac disorders such as acute cardiac injury within the first few hours of clinical presentation. A need thereof exists for such an early marker.

More recently, it has been suggested that BNP-SP may be useful in diagnosing heart disease (US 2005/0244904, WO 2005/052593). It is generally indicated that levels of BNP-SP will be higher in heart failure patients than normal patients. No time course information as to when to measure BNP-SP levels is provided. It is stated that BNP-SP levels are elevated in conjunction with N-BNP.

It is an object of the present invention to go some way towards fulfilling the need for an early marker of acute cardiac disorders, and/or to at least provide the public with a useful choice.

SEQUENCE LISTING

The instant application contains a Sequence Listing which has been submitted in ASCII format via EFS-Web and is hereby incorporated by reference in its entirety. Said ASCII copy, created on Mar. 18, 2013, is named OTA-2001-CT_SL.txt and is 19,408 bytes in size.

SUMMARY OF THE INVENTION

Human B-type natriuretic signal peptide (BNP-SP) or preproBNP (1-26) is a 26 amino acid peptide cleaved from preproBNP (1-134) SEQ ID NO:1. BNP-SP is shown separately in SEQ ID NO:21.

The applicants have surprisingly discovered that the circulating concentration of BNP-SP is highest in the first few hours following onset of, or at clinical presentation with suspected acute coronary syndromes (ACS). Peaks are in the order of four to ten times higher, commonly five to eight times higher than normal control populations in these first hours.

Accordingly, in a first aspect the present invention provides a method for predicting, diagnosing or monitoring an acute cardiac disorder (ACD) in a subject, the method comprising: measuring the level of BNP-SP in a biological sample obtained from the subject within two hours of onset of the ACD, or within two hours of presentation with the ACD; and comparing the level of said BNP-SP with the BNP-SP level from a control wherein a measured level of BNP-SP higher than the control level is indicative of ACD.

The invention also provides a method for monitoring a response to treatment of an acute cardiac disorder (ACD) in a subject, the method comprising measuring the level of BNP-SP in a biological sample obtained from the subject within two hours of onset of the ACD or within two hours of presentation with the ACD; and comparing the level of said BNP-SP with the BNP-SP level from a control, wherein a change in the measured level of BNP-SP from the control level is indicative of a response to the treatment.

In another aspect, the invention also provides a method for predicting, diagnosing or monitoring a cardiac transplant rejection episode in a subject, the method comprising measuring the level of BNP-SP in a biological sample obtained from a subject within two hours of heart transplant and comparing the level of said BNP-SP with the BNP-SP level from a control, wherein a measured level of BNP-SP higher than the control level is indicative of transplant rejection.

The invention also provides a method of distinguishing between a pulmonary disorder and an acute cardiac disorder (ACD) in a subject, the method comprising measuring the level of BNP-SP in a biological sample obtained from a subject within two hours of presentation with the disorder; and comparing the level of said BNP-SP with the BNP-SP level from a control wherein a measured level of BNP-SP higher than the control level is indicative of ACD.

The invention also provides a method for predicting, diagnosing or monitoring an acute cardiac disorder (ACD), cardiac transplant rejection, or ACD/pulmonary disorder in a subject, the method comprising measuring the level of BNP-SP in a biological sample obtained from the subject within the first two hours of onset of, or clinical presentation with ACD, cardiac transplant rejection or ACD/pulmonary disorder.

Preferably, the measured level of BNP-SP is compared with the BNP-SP level from a control wherein a measured level of BNP-SP higher than the control level is indicative of ACD or cardiac transplant rejection.

Preferably, the methods of the invention are in vitro methods.

In one embodiment, the measurement of BNP-SP levels is carried out within one hour, of onset or clinical presentation, preferably within 30 minutes.

Preferably, the biological sample is blood, saliva, interstitial fluid, plasma, urine, serum or heart tissue.

In one embodiment, the measuring step comprises detecting binding between BNP-SP and a binding agent that selectively binds BNP-SP. The binding agent is preferably an antibody or antibody fragment. Most commonly, the antibody is a monoclonal, polyclonal or humanized antibody. Monoclonal antibodies are preferred In an alternate embodiment, the levels of BNP-SP are measured using mass spectroscopy.

The BNP-SP which is selectively bound by the antibody is the full length human BNP-SP molecule (SEQ ID NO:21) or an antigenic variant or fragment thereof. Preferably, the fragment is at least five amino acids in length. Desirably, the antibody binds the N-terminus or the C-terminus of BNP-SP.

Specific antigenic peptides which the binding agent selectively binds include human BNP-SP (1-10) (SEQ ID NO:13), BNP-SP (1-17) (SEQ ID NO:15), BNP-SP (3-15) (SEQ ID NO:23), BNP-SP (17-26) (SEQ ID NO:19), BNP-SP (12-23) (SEQ ID NO:17) and BNP-SP (1-26) (SEQ ID NO:21) or variants thereof.

Binding of BNP-SP is preferably measured using antibodies or antibody fragments that are immobilised on a solid phase.

Levels of BNP-SP may usefully be measured with an assay selected from RIA, ELISA, fluoroimmunoassay, immunofluorometric assay, mass spectrometry and immunoradiometric assay.

Accordingly, the invention also provides an assay for BNP-SP in a biological sample obtained from a subject within two hours from onset of, or within two hours of clinical presentation with ACD, cardiac transplant rejection, or ACD/pulmonary disorder, the assay comprising detecting and measuring the level of BNP-SP in the sample using any known methods.

Preferably, the assay is an in vitro assay.

The methods of the invention may further comprise measuring the level of one or more non-BNP-SP markers of said ACD, or cardiac transplant rejection, or ACD/pulmonary disorder and comparing the levels against marker levels from a control wherein a deviation in the measured level from the control level of non-BNP-SP marker, together with a measured level of BNP-SP which is higher than the control level of BNP-SP, is predictive or diagnostic of the ACD, or can be used to monitor said ACD, cardiac transplant rejection or ACD/pulmonary disorder.

Markers for use in the context of acute coronary syndrome include troponin T, troponin I, creatine kinase MB, myoglobin, BNP, NT-BNP, LDH, aspartate aminotransferase, and heart specific fatty acid binding protein (H-FABP).

In another aspect, the present invention also provides a BNP-SP binding agent that selectively binds BNP-SP or an antigenic fragment or variant thereof for use in predicting, diagnosing or monitoring an acute cardiac disorder (ACD), cardiac transplant rejection or ACD/pulmonary disorder in a subject, wherein the ACD, cardiac transplant rejection or ACD/pulmonary disorder is characterised by the appearance of BNP-SP in a biological sample obtained from the subject within two hours of onset of, or within two hours of clinical presentation with ACD, cardiac transplant rejection or ACD/pulmonary disorder.

In one embodiment, the binding agent is preferably an antibody or fragment thereof.

In another embodiment, the binding agent is any solid or non-solid material capable of binding BNP-SP.

The invention is also directed to the use of BNP-SP binding agent in the manufacture of a prognostic, diagnostic or monitoring tool for assessing an acute cardiac disorder (ACD), cardiac transplant rejection or ACD/pulmonary disorder in a subject, wherein assessment is carried out within two hours of onset of, or within two hours of clinical presentation with ACD, cardiac transplant rejection or ACD/pulmonary disorder.

The invention also relates to a use of the invention wherein the prognostic, diagnostic or monitoring tool is calibrated to measure BNP-SP levels in the range of from 0.1 to 500 pmol/L, preferably 1 to 400 pmol/L, preferably 10 to 350 pmol/L, preferably 20 to 300 pmol/L, preferably 25 to 250 pmol/L, preferably 30 to 180 pmol/L, preferably 35 to 150 pmol/L, and preferably 40 to 120 pmol/L.

In another aspect, the invention provides a kit for predicting, diagnosing or monitoring an acute cardiac disorder (ACD), cardiac transplant rejection or ACD/pulmonary disorder comprising a BNP-SP binding agent of the invention, wherein the kit is for use with a biological sample obtained from a subject within two hours of onset of, or clinical presentation with ACD, cardiac transplant rejection or ACD/pulmonary disorder.

The invention also provides a kit for predicting, diagnosing or monitoring an acute cardiac disorder (ACD) comprising a binding agent of the invention, wherein the kit is calibrated to measure BNP-SP levels in the range of 0.1 to 500 pmol/L, preferably 1 to 400 pmol/L, preferably 10 to 350 pmol/L, preferably 20 to 300 pmol/L, preferably 25 to 250 pmol/L, preferably 30 to 180 pmol/L, preferably 35 to 150 pmol/L, and preferably 40 to 120 pmol/L.

Preferably, the kit also includes instructions for predicting, diagnosing or monitoring ACD, cardiac transplant rejection, or ACD/pulmonary disorder in a subject within two hours of onset, or clinical presentation, from the BNP-SP level measured in the biological sample obtained within two hours of onset or clinical presentation.

In another aspect, the invention relates to a nucleic acid molecule encoding a BNP-SP of the invention wherein said nucleic acid is selected from
(a) SEQ ID NO:14;
(b) SEQ ID NO:16;
(c) SEQ ID NO:18;
(d) SEQ ID NO:20;
(e) a complement of any one of (a) to (d);
(f) a sequence of at least 15 nucleotides in length, capable of hybridising to the sequence of any one of (a) to (e) under stringent conditions with the proviso that the sequence is not ccagtgcacaagctgcttggggaggcgaga (SEQ ID NO: 25) or SEQ ID NO: 22.

The invention also provides a genetic construct comprising a nucleic acid molecule of the invention, a vector comprising the genetic construct, a host cell comprising the genetic construct or vector, a polypeptide encoded by a nucleic acid molecule of the invention, an antibody which selectively binds a polypeptide of the invention, and a method for recombinantly producing a polypeptide of the invention.

Accordingly, in another aspect the invention provides an isolated BNP-SP polypeptide selected from
(a) SEQ ID NO:13;
(b) SEQ ID NO:15;
(c) SEQ ID NO:17; and
(d) SEQ ID NO:19.

BRIEF DESCRIPTION OF THE DRAWINGS

The invention will now be described with reference to the figures in the accompanying drawings in which Figures FIG. 1 is a schematic diagram outlining the processing of human preproBNP resulting in generation of free signal, N-BNP and BNP peptides;

FIG. 2A is a single letter notation format of preproBNP sequences in seven species (SEQ IN NOS 1, 3, 5, 7, 9 and 11-12, respectively, in order of appearance). The signal peptide region is in bold and underlined;

FIG. 2B is a Clustal W version 1.83 JALVIEW multiple sequence alignment of the prepoBNP signal peptide sequences (SEQ ID NOS 21 and 26-31, respectively, in order of appearance). The default Clustal W parameters were used in this alignment as follows: DNA Gap Open Penalty=15.0; DNA Gap Extension Penalty=6.66; DNA matrix=Identity; Protein Gap Open Penalty=10.0; Protein Gap Extension Penalty=0.2; Protein Matrix=Gonnet; Protein/DNA END-GAP=−1; Protein/DNA GAPDIST=4. The amino acids were submitted in the Pearson (fasta) format.[9]

FIG. 8. Shows a table of cross reactivity data of BNP-SP antiserum; and

DEFINITIONS

Figure 3:
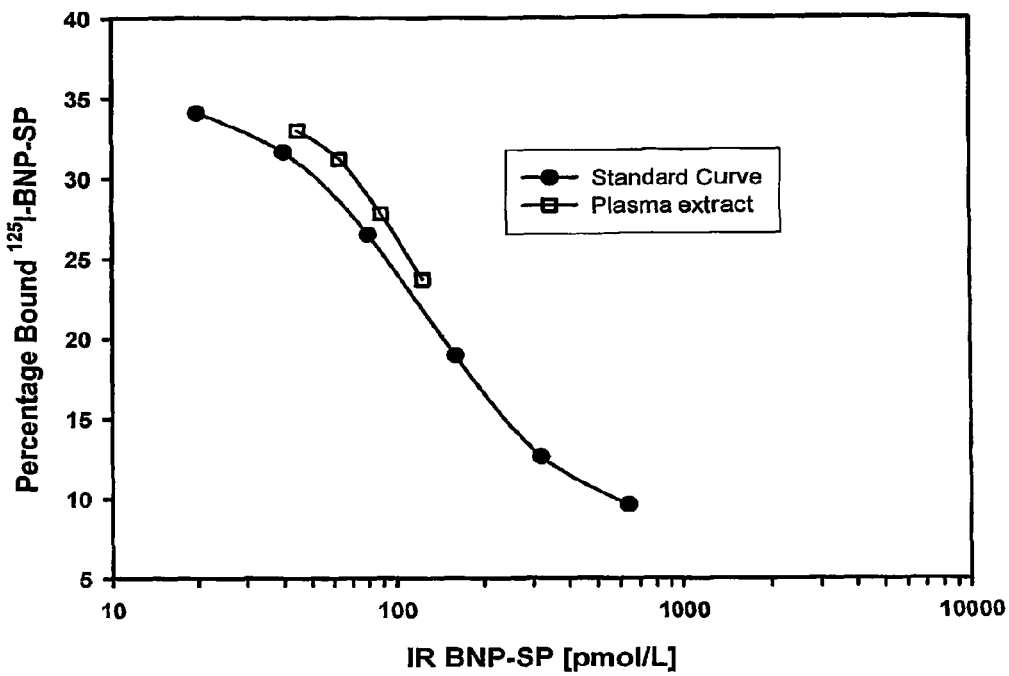
FIG. 3 shows the results of a radioimmunoassay with human plasma extracts (open squares) dilute in parallel with the BNP-SP standard curve (filled circles)

Acute Cardiac Disorder (ACD), includes but is not limited to: acute coronary syndromes: (AMI) with ST-elevation on presenting ECG, unstable angina, and acute non ST-elevated MI; cardiac ischemia; acute cardiac injury; acute cardiac damage resulting from acute drug toxicity, acute cardiomyopathies, and cardiac transplant rejection. Full descriptive, definitions of these disorders are found in reference 1.

ACD/pulmonary disorder refers to a subject with an undiagnosed, or suspected ACD or pulmonary disorder.

Acute coronary syndromes (ACS) encompasses a wide spectrum of cardiac ischemia events including unstable angina, acute myocardial infarct with ST-elevation on presenting electrocardiogram (ECG), and acute myocardial infarction without ST-segment elevation on ECG.

The term "antibody" refers to an immunoglobulin molecule having a specific structure that interacts (binds) specifically with a molecule comprising the antigen used for synthesizing the antibody or with an antigen closely related to it. An antibody binds selectively or specifically to a BNP-SP polypeptide of the invention if the antibody binds preferentially to the BNP-SP e.g. has less than 25%, preferably less than 10%, preferably less than 1% cross-reactivity with a non-BNP-SP polypeptides. Usually, the antibody will have a binding affinity (dissociation constant (Kd) value), for the antigen of no more than $10^{-7}$M, preferably less than about $10^{-8}$M, preferably less than about $10^{-9}$M. Binding affinity may be assessed using surface plasma resonance.

Biological sample as used herein means any sample derived from a subject to be screened. The sample may be any sample known in the art in which the BNP-SP can be detected. Included are any body fluids such as plasma, blood, saliva, interstitial fluid, serum, urine, synovial, cerebrospinal, lymph, seminal, amniotic, pericardial fluid and ascites, as well as tissues such as cardiac tissues but not limited thereto. Also included are samples from normal healthy subjects with no clinical history of acute cardiac disorders.

The term BNP-SP refers to the complete 26 amino acid BNP signal peptide for the human prepro BNP sequence (SEQ ID NO: 1) BNP-SP is shown separately in SEQ ID NO:21. Also encompassed within the term BNP-SP is a variant or fragment of BNP-SP.

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "polynucleotide(s)," as used herein, means a single or double-stranded deoxyribonucleotide or ribonucleotide polymer of any length, and include as non-limiting examples, coding and non-coding sequences of a gene, sense and antisense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, fragments, genetic constructs, vectors and modified polynucleotides. Reference to a nucleic acid molecule is to be similarly understood.

A "fragment" of a polynucleotide sequence provided herein is a subsequence of contiguous nucleotides that is capable of specific hybridization to a target of interest, e.g., a sequence that is at least 10 nucleotides in length. The fragments of the invention comprise 10, preferably 15 nucleotides, preferably 16, preferably 17, preferably 18, preferably 19, preferably 21, preferably 22, preferably 23, preferably 24, preferably 25, preferably 26, preferably 27, preferably 28, preferably 29, preferably 30, preferably 31, preferably 32, preferably 33, preferably 34, preferably 35, preferably 36, preferably 37, preferably 38, preferably 39, preferably 40, preferably 41, preferably 42, preferably 43, preferably 44, preferably 45, preferably 46, preferably 47, preferably 48, preferably 49, preferably 50, preferably 51, preferably 52, preferably 53, preferably 54, preferably 55, preferably 56, preferably 57, preferably 58, preferably 59, preferably 60, preferably 61, preferably 62, preferably 63, preferably 64, preferably 65, preferably 66, preferably 67, preferably 68, preferably 69, preferably 70, preferably 71, preferably 72, preferably 73, preferably 74, preferably 75, preferably 76, preferably 77 contiguous nucleotides of a polynucleotide of SEQ ID NO:22. A fragment of a polynucleotide sequence can be used as a primer, a probe, included in a microarray, or used in polynucleotide-based selection methods herein.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

The term "polypeptide", as used herein, encompasses amino acid chains of any length, but preferably at least 5 amino acids, preferably at least 6, preferably at least 7, preferably at least 8, preferably at least 9, preferably at least 10, preferably at least 11, 12, preferably at least 13, preferably at least 14, preferably at least 15, preferably at least 16, preferably at least 17, preferably at least 18, preferably at least 19, preferably at least 20, preferably at least 21, preferably at least 22, preferably at least 23, preferably at least 24, preferably at least 25, and preferably all 26 amino acids of the full-length BNP-SP protein (SEQ ID NO:21), in which amino acid residues are linked by covalent peptide bonds. Polypeptides useful in the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity or binding and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above signal peptide activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques. The polynucleotide or polypeptide sequences may be prepared by at least one purification step.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the polypeptides useful in the invention and biological activities that are the same or similar to those of the parent polypeptides or polynucleotides. The term "variant" with reference to polynucleotides and polypeptides encompasses all forms of polynucleotides and polypeptides as defined herein.

Variant polynucleotide sequences preferably exhibit at least 50%, at least 60%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% identity to a sequence of the present invention. Identity is found over a comparison window of at least 10 nucleotide positions, preferably at least 15 nucleotide positions, preferably at least 20 nucleotide positions, preferably at least 27 nucleotide positions, preferably at least 40 nucleotide positions, preferably at least 50 nucleotide positions, and most preferably over the entire length of a polynucleotide of the invention.

Polynucleotide sequence identity may be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http://www.hgmp.mrc.ac.uk/Software/EMBOSS/. The European Bioinformatics Institute server also provides the facility to perform EMBOSS-needle global alignments between two sequences on line at http:/www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

Polynucleotide variants also encompass those which exhibit a similarity to one or more of the specifically identified sequences that is likely to preserve the functional equivalence of those sequences and which could not reasonably be expected to have occurred by random chance. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-5}$, more preferably less than $1\times10^{-6}$, more preferably less than $1\times10^{-9}$, more preferably less than $1\times10^{-12}$, more preferably less than $1\times10^{-15}$, more preferably less than $1\times10^{-18}$ and most preferably less than $1\times10^{-21}$ when compared with any one of the specifically identified sequences.

Use of BLASTN is preferred for use in the determination of sequence identity for polynucleotide variants according to the present invention.

The identity of polynucleotide sequences may be examined using the following UNIX command line parameters:
bl2seq -i nucleotideseq1 -j nucleotideseq2 -F F -p blastn
The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity and similarity can also be determined in the following manner. The subject polynucleotide sequence is compared to a candidate polynucleotide sequence using sequence alignment algorithms and sequence similarity search tools such as in Genbank, EMBL, Swiss-PROT and other databases. Nucleic Acids Res 29:1-10 and 11-16, 2001 provides examples of online resources. BLASTN (from the BLAST suite of programs, version 2.2.13 Mar. 2007 in bl2seq (Tatiana A. et al, FEMS Microbiol Lett. 174:247-250 (1999), Altschul et al., Nuc. Acid Res 25:3389-3402, (1997)), which is publicly available from NCBI (ftp://ftp.ncbi.nih.gov/blast/) or from NCB1 at Bethesda, Md., USA. The default parameters of bl2seq are utilized except that filtering of low complexity parts should be turned off.

Alternatively, variant polynucleotides hybridize to the specified polynucleotide sequence, or a complement thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing, incorporated herein by reference). Tm for polynucleotide molecules greater than about 100 bases can be calculated by the formula Tm=81.5+0.41% (G+C−log(Na+) (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for a polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

In one embodiment stringent conditions use 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulphate at 42° C., with washes at 42° C. in 0.2×SSC and 50% formamide at 55° C., followed by a wash comprising of 0.1×SSC containing EDTA at 55° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the bl2seq program via the tblastx algorithm as described above.

The term "variant" with reference to polypeptides also encompasses naturally occurring, recombinantly and synthetically produced polypeptides. Variant polypeptide sequences preferably exhibit at least 50%, preferably at least 60%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% identity to a sequence of the present invention. Identity is found over a comparison window of at least 5 amino acid positions, preferably at least 7 amino acid positions, preferably at least 10 amino acid positions, preferably at least 15 amino acid positions, preferably at least 20 amino acid positions and most preferably over the entire length of a polypeptide used in the invention.

Polypeptide variants also encompass those which exhibit a similarity to one or more of the specifically identified sequences that is likely to preserve the functional equivalence of those sequences and which could not reasonably be expected to have occurred by random chance.

Polypeptide sequence identity and similarity can be determined in the following manner. The subject polypeptide sequence is compared to a candidate polypeptide sequence using BLASTP (from the BLAST suite of programs, version 2.2.14 [May 2006]) in bl2seq, which is publicly available from NCBI (ftp://ftp.ncbi.nih.gov/blast/). The default parameters of bl2seq are utilized except that filtering of low complexity regions should be turned off.

The similarity of polypeptide sequences may be examined using the following UNIX command line parameters:

bl2seq -i peptideseq1 -j peptideseq2 -F F -p blastp

Variant polypeptide sequences preferably exhibit an E value of less than $1\times10^{-5}$, more preferably less than $1\times10^{-6}$, more preferably less than $1\times10^{-9}$, more preferably less than $1\times10^{-12}$, more preferably less than $1\times10^{-15}$, more preferably less than $1\times10^{-18}$ and most preferably less than $1\times10^{-21}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Polypeptide sequence identity may also be calculated over the entire length of the overlap between a candidate and subject polypeptide sequences using global sequence alignment programs. EMBOSS-needle (available at http:/www.e-bi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Use of BLASTP as described above is preferred for use in the determination of polypeptide variants according to the present invention.

Preferred variants include peptides who's sequence differs from the human BNP-SP (1-26) herein by one or more conservative amino acid substitutions, deletions, additions or insertions which do not affect the biological activity of the peptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagines, glutamine; serine, threonine; lysine, arginine; and phenylalanine, tyrosine. Examples of conservative substations can also be found in the sequences of BNP-SP in FIGS. 2A and 2B whereby the substitutions in different mammalian species compared to the human sequence are shown. Other conservative substitutions can be taken from Table 1 below.

TABLE 1

| Original Residue | Exemplary Substitutions | Preferred Substitution |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg:
(5) residues that influence chain orientation: gly, pro; and
(6) aromatic: trp, tyr, phe.

Non-conservative substitutions will entail exchanging a member of one of these classes for a member of another class. See for example R being substituted with H at BNP-SP 25.

Other variants include peptides with modifications which influence peptide stability. Such analogs may contain, for example, one or more non-peptide bonds (which replace the peptide bonds) in the peptide sequence. Also included are analogs that include residues other than naturally occurring L-amino acids, e.g. D-amino acids or non-naturally occurring synthetic amino acids, e.g. beta or gamma amino acids and cyclic analogs.

Substitutions, deletions, additions or insertions may be made by mutagenesis methods known in the art. A skilled worker will be aware of methods for making phenotypically silent amino acid substitutions. See for example Bowie et al., 1990, Science 247, 1306.[10]

Also included within the polypeptides of the invention are those which have been modified during or after synthesis for example by biotinylation, benzylation, glycosylation, phosphorylation, amidation, by derivatization using blocking/protecting groups and the like. Such modifications may increase stability or activity of the polypeptide.

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:
 a) a promoter functional in the host cell into which the construct will be transformed,
 b) the polynucleotide to be expressed, and
 c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences and/or other regulatory elements.

"Operably-linked" means that the sequence to be expressed is placed under the control of regulatory elements that include promoters, transcription control sequences, translation control sequences, origins of replication, tissue-specific regulatory elements, temporal regulatory elements, enhancers, polyadenylation signals, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

"Subject" as used herein is preferably a mammal and includes human, and non-human mammals such as cats, dogs, horses, cows, sheep, deer, mice, rats, primates (including gorillas, rhesus monkeys and chimpanzees), possums and other domestic farm or zoo animals. Preferably, the mammal is human.

The term "presentation" as used herein refers to presentation of a subject at a medical facility such as a clinic or hospital.

The term "treat", "treating" or "treatment" and "preventing" refer to therapeutic or prophylactic measures which alleviate, ameliorate, manage, prevent, restrain, stop or reverse progression of ACD, or cardiac transplant rejection or effects thereof, particularly of ACS. The subject may show observable or measurable (statistically significant) reduction in one or more of TnI, BNP, N-BNP, and other usual clinical markers known to those skilled in the art, indicating improvement.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

DETAILED DESCRIPTION OF THE INVENTION

Human B-type natriuretic peptide (BNP) is a member of the cardiac natriuretic peptide family. As shown in FIG. 1, preproBNP is a 134 amino acid molecule. The signal peptide BNP-SP (1-26) is cleaved to give preproBNP (27-134). PreproBNP (27-134) is in turn further processed to give bioactive forms preproBNP (103-134) and prepro BNP (27-102). It is likely that BNP-SP is degraded into smaller fragments by signal peptidase (SPP); usually near the hydrophobic central region of the BNP-SP (1-26) sequence.

It has long been thought that the functional role of the BNP-SP is limited to controlling the trafficking of BNP in the endoplasmic reticulum. Once this is achieved it has been assumed that the signal peptide is then degraded without ever being secreted from the cell.

Very recently, it has been found that BNP-SP appears in the circulation (WO 2005/052593; US 2005/0244904). Based on this finding BNP-SP has been suggested for use as a circulating biomarker for cardiac disease. The present applicants have made a further and highly unexpected finding. In patients with acute myocardial infarction (AMI) the circulating concentration of BNP-SP is highest in the first few hours following the onset of the patient's symptoms—in fact, at the time of presentation to the hospital or clinic. This is contrary to expectations that BNP-SP levels would be correlated with N-BNP levels and could therefore be expected to reach their peak 12 to 24 hours from onset of, or clinical presentation with ACD, cardiac transplant rejection, or with an undiagnosed or suspected ACD or pulmonary disorder. Levels observed in the first few hours are surprisingly very high often reaching a peak some four to ten, commonly five to eight fold higher than levels in a normal control population.

The level of BNP-SP remains up to three times higher than BNP-SP levels in a control population for at least 6 weeks from first measurement on clinical presentation. These findings suggest BNP-SP is useful as a very clear early stage marker of cardiac transplant rejection, ACD including acute coronary syndromes (ACS) such as AMI, particularly non-ST elevated MI, acute cardiac ischemia and may be used to distinguish ACD from pulmonary disorders.

Based on these surprising findings, the applicants have determined for the first time, that it would be useful to screen for circulating BNP-SP or variants or fragments thereof, as well as nucleotide sequences encoding BNP-SP or the variants and fragments thereof in a biological sample taken from a subject within two hours of onset of, or at clinical presentation with the disorder.

Useful in the invention are antigenic fragments or variants of BNP-SP which are least 5 amino acids in length. Particularly useful fragments are the N-terminus or C-terminus of BNP-SP. Examples of specific antigenic peptides are BNP-SP (1-10) (SEQ ID NO:13), BNP-SP (1-17) (SEQ ID NO:15), BNP-SP (12-23) (SEQ ID NO:17), and BNP-SP (17-26) (SEQ ID NO:19). Corresponding nucleotide sequences are given in SEQ ID NOs: 14, 16, 18 and 20 respectively. These sequences are provided by the applicants for the first time. Both the nucleic acid molecules and peptides form aspects of the invention.

Accordingly, in a first aspect, the invention provides a nucleic acid molecule encoding a BNP-SP of the invention selected from
 (a) SEQ ID NO:14;
 (b) SEQ ID NO:16;
 (c) SEQ ID NO:18;
 (d) SEQ ID NO:20;
 (e) a complement of any one of (a) to (d);
 (f) a sequence of at least 15 nucleotides in length, capable of hybridising to the sequence of any one of (a) to (e) under stringent conditions with the proviso that the sequence is not ccagtgcacaagctgcttggggaggcgaga (SEQ ID NO: 25) or SEQ ID NO: 22.

The invention also provides isolated BNP-SP polypeptides encoded by a nucleic acid molecule of the invention.

Specific polypeptides of the invention include polypeptides having the amino acid sequences of SEQ ID NOs: 13, 15, 17 and 19 all as set forth in the accompanying sequence listing. Also contemplated are functionally equivalent variants and fragments of these polypeptides as defined herein.

The nucleic acid molecules of the invention or otherwise described herein are preferably isolated. They can be isolated from a biological sample using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser. The nucleic acid molecules of the invention can be amplified using primers, as defined herein, derived from the polynucleotide sequences of the invention.

Further methods for isolating polynucleotides include use of all, or portions of, the polynucleotide of the invention, particularly a polynucleotide having the sequence set forth in SEQ ID NO:19 as hybridization probes. The technique of hybridizing labeled polynucleotide probes to polynucleotides immobilized on solid supports such as nitrocellulose filters or nylon membranes, can be used to screen genomic or cDNA libraries. Similarly, probes may be coupled to beads and hybridized to the target sequence. Isolation can be effected using known art protocols such as magnetic separation. Exemplary stringent hybridization and wash conditions are as given above.

Polynucleotide fragments may be produced by techniques well-known in the art such as restriction endonuclease digestion and oligonucleotide synthesis.

A partial polynucleotide sequence may be used as a probe, in methods well-known in the art to identify the corresponding full length polynucleotide sequence in a sample. Such methods include PCR-based methods, 5'RACE (Methods Enzymol. 218: 340-56 (1993); Sambrook et al., Supra) and hybridization-based method, computer/database-based methods. Detectable labels such as radioisotopes, fluorescent, chemiluminescent and bioluminescent labels may be used to facilitate detection. Inverse PCR also permits acquisition of unknown sequences, flanking the polynucleotide sequences disclosed herein, starting with primers based on a known region (Triglia et al., Nucleic Acids Res 16, 8186, (1998)) The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Supra). Primers and primer pairs which allow amplification of polynucleotides of the invention, also form a further aspect of this invention.

Variants (including orthologues) may be identified by the methods described. Variant polynucleotides may be identified using PCR-based methods (Mullis et al., Eds. 1994 The Polymerase Chain Reaction, Birkhauser). Typically, the polynucleotide sequence of a primer, useful to amplify variants of polynucleotide molecules by PCR, may be based on a sequence encoding a conserved region of the corresponding amino acid sequence.

Further methods for identifying variant polynucleotides include use of all, or portions of, the specified polynucleotides as hybridization probes to screen genomic or cDNA libraries as described above. Typically probes based on a sequence encoding a conserved region of the corresponding amino acid sequence may be used. Hybridisation conditions may also be less stringent than those used when screening for sequences identical to the probe.

The variant sequences, including both polynucleotide and polypeptide variants, may also be identified by the computer-based methods discussed above.

Multiple sequence alignments of a group of related sequences can be carried out with CLUSTALW (Thompson, et al., Nucleic Acids Research, 22:4673-4680 (1994), http://www-igbmc.u-strasbg.fr/BioInfo/ClustalW/Top.html) or T-COFFEE (Cedric Notredame et al., J. Mol. Biol. 302: 205-217 (2000))) or PILEUP, which uses progressive, pairwise alignments. (Feng et al., J. Mol. Evol. 25, 351 (1987)).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch et al., Nucleic Acids Res. 22, 3583 (1994); Hofmann et al., Nucleic Acids Res. 27, 215 (1999)) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., Nucleic Acids Res. 30, 235 (2002)). Prosearch is a tool that can search SWISS-PROT and EMBL databases with a given sequence pattern or signature.

Proteins can be classified according to their sequence relatedness to other proteins in the same genome (paralogues) or a different genome (orthologues). Orthologous genes are genes that evolved by speciation from a common ancestral gene and normally retain the same function as they evolve. Paralogous genes are genes that are duplicated within a genome and genes may acquire new specificities or modified functions which may be related to the original one. Phylogenetic analysis methods are reviewed in Tatusov et al., Science 278, 631-637, 1997).

In addition to the computer/database methods described above, polypeptide variants may be identified by physical methods, for example by screening expression libraries using antibodies raised against polypeptides of the invention (Sambrook et al., Molecular Cloning: A Laboratory Manual, 2nd Ed. Cold Spring Harbor Press, 1987) by recombinant DNA techniques also described by Sambrook et al. or by identifying polypeptides from natural sources with the aid of such antibodies.

Polypeptides, including variant polypeptides, may be prepared using peptide synthesis methods well known in the art such as direct peptide synthesis using solid phase techniques (e.g. Merrifield, 1963, in J. Am. Chem. Soc. 85, 2149; Stewart et al., 1969, in Solid-Phase Peptide Synthesis, WH Freeman Co, San Francisco Calif.; Matteucci et al. J. Am. Chem. Soc. 103:3185-3191, 1981) or automated synthesis, for example using a Synthesiser from Applied Biosystems (California, USA). Mutated forms of the polypeptides may also be produced using synthetic methods such as site-specific mutagensis of the DNA encoding the amino acid sequence as described by Adelmen et al; DNA 2, 183 (1983).

The polypeptides and variant polypeptides herein are preferably isolated. They may be isolated or purified from natural sources using a variety of techniques that are well known in the art (e.g. Deutscher, 1990, Ed, Methods in Enzymology, Vol. 182, *Guide to Protein Purification,*). Technologies include HPLC, ion-exchange chromatography, and immunochromatography but are not limited thereto.

Alternatively the polypeptides and variant polypeptides may be expressed recombinantly in suitable host cells and separated from the cells as discussed below. The polypeptides and variants have utility in generating antibodies, and generating ligands amongst other uses.

The genetic constructs described herein may comprise one or more of the disclosed polynucleotide sequences and/or polynucleotides encoding the disclosed polypeptides, of the invention and may be useful for transforming, for example, bacterial, fungal, insect, mammalian or plant organisms. The genetic constructs of the invention are intended to include expression constructs as herein defined. Included are vectors (such as pBR322, pUC18, pU19, Mp18, Mp19, ColE1, PCR1 and pKRC), phages (such as lambda gt10), and M13 plasmids (such as pBR322, pACYC184, pT127, RP4, p1J101, SV40 and BPV), cosmids, YACS, BACs shuttle vectors such as pSA3, PAT28 transposons (such as described in U.S. Pat. No. 5,792,294) and the like.

The constructs may conveniently include a selection gene or selectable marker. Typically an antibiotic resistance marker such as ampicillin, methotrexate, or tetracycline is used.

Promoters useful in the constructs include β-lactamase, alkaline phosphatase, tryptophan, and tac promoter systems which are all well known in the art. Yeast promoters include 3-phosphoglycerate kinase, enolase, hexokinase, pyruvate decarboxylase, glucokinase, and glyceraldehydrate-3-phosphanate dehydrogenase but are not limited thereto.

Enhancers may also be employed to act on the promoters to enhance transcription. Suitable enhancers for use herein include SV40 enhancer, cytomeglovirus early promoter enhancer, globin, albumin, insulin and the like.

Methods for producing and using genetic constructs and vectors are well known in the art and are described generally in Sambrook et al., (supra), and Ausubel et al., Current Protocols in Molecular Biology, Greene Publishing, 1987. Methods for transforming selected host cells with the vectors are also known, for example, the calcium chloride treatment described by Cohen, S N; PNAS 69, 2110, 1972.

Host cells comprising the genetic constructs and vectors described may be derived from prokaryotic or eukaryotic sources, for example yeast, bacteria, fungi, insect (eg baculovirus), animal, mammalian or plant organisms. In one embodiment the host cells are isolated host cells. Prokaryotes most commonly employed as host cells are strains of *E. coli*. Other prokaryotic hosts include *Pseudomonas, Bacillus, Serratia, Klebsiella, Streptomyces, Listeria, Saccharomyces, Salmonella* and *Mycobacteria* but are not limited thereto.

Eukaryotic cells for expression of recombinant protein include but are not limited to Vero cells, HeLa, CHO (Chinese Hamster ovary cells), 293, BHK cells, MDCK cells, and COS cells as well as prostate cancer cell lines such as PrEC, LNCaP, Du 145 and RWPE-2. The cells are available from ATCC, Virginia, USA.

Prokaryotic promoters compatible with expression of nucleic acid molecules of the invention include known art constitutive promoters (such as the int promoter of bacteriophage lamda and the bla promoter of the beta-lactamase gene sequence of pBR322) and regulatable promoters (such as lacZ, recA and gal). A ribosome binding site upstream of the coding sequence may also be required for expression.

Host cells comprising genetic constructs, such as expression constructs, are useful in methods for recombinant production of polypeptides. Such methods are well known in the art (see for example Sambrook et al. supra). The methods commonly involve the culture of host cells in an appropriate medium in conditions suitable for or conducive to, expression and selection of a polypeptide of the invention. Cells with a selectable marker may additionally be grown on medium appropriate for selection of host cells expressing a polypeptide of the invention. Transformed host cells expressing a polypeptide of the invention are selected and cultured under conditions suitable for expression of the polypeptide. The expressed recombinant polypeptide, may be separated and purified from the culture medium using methods well known in the art including ammonium sulfate precipitation, ion exchange chromatography, gel filtration, affinity chromatography, electrophoresis and the like (e.g. Deutscher, Ed, 1990, Methods in Enzymology, Vol 182, Guide to Protein Purification). Host cells may also be useful in methods for production of a product generated by an expressed polypeptide of the invention.

In another aspect, the present invention provides a method for predicting, diagnosing or monitoring an acute cardiac disorder (ACD) in a subject, the method comprising: measuring the level of BNP-SP in a biological sample obtained from the subject within two hours of onset of the ACD, or within two hours of presentation with ACD; and comparing the level of said BNP-SP with the BNP-SP level from a control wherein a measured level of BNP-SP higher than the control level is indicative of ACD.

In another aspect the invention provides a method for monitoring a response to treatment of a an acute cardiac disorder (ACD) in a subject, the method comprising measuring the level of BNP-SP in a biological sample obtained from the subject within two hours of onset of the ACD, or within two hours of presentation with the ACD; and comparing the level of said BNP-SP with the BNP-SP level from a control, wherein a change in the measured level of BNP-SP from the control level is indicative of a response to the treatment.

It is known in the art that BNP precursors such as proBNP27-102 proBNP27-47, can be used in predicting or diagnosing a cardiac transplant rejection episode and to distinguish between pulmonary and cardiovascular causes of dyspnea (shortness of breath). See US 2005/0244902. Accordingly, it is similarly predictable that BNP-SP can be used as an early marker of cardiac transplant rejection based on cardiac tissue analysis, and to distinguish pulmonary from acute cardiac disorders.

Accordingly, the invention also provides a method for predicting, diagnosing or monitoring a cardiac transplant rejection episode in a subject, the method comprising measuring the level of BNP-SP in a biological sample obtained from a subject within two hours of heart transplant and comparing the level of said BNP-SP with the BNP-SP level from a control, wherein a measured level of BNP-SP higher than the control level is indicative of transplant rejection.

The invention also provides a method of distinguishing between a pulmonary disorder and an acute cardiac disorder (ACD) in a subject, the method comprising measuring the level of BNP-SP in a biological sample obtained from a subject within two hours of presentation with the disorder; and comparing the level of said BNP-SP with the BNP-SP level from a control wherein a measured BNP-SP level higher than the control level is indicative of ACD.

In one embodiment, the invention provides a method for predicting, diagnosing or monitoring an acute cardiac disorder (ACD), cardiac transplant rejection, or ACD/pulmonary disorder in a subject, the method comprising measuring the level of BNP-SP in a biological sample obtained from the subject within the first two hours of onset of, or clinical presentation with ACD, transplant rejection or ACD/pulmonary disorder.

Preferably, the measured level of BNP-SP is compared with the BNP-SP level from a control wherein a measured level of BNP-SP higher than the control level is indicative of ACD or transplant rejection.

The skilled reader will appreciate that for evaluation purposes, marker requires correlation with a reference valve or control value.

As used herein a control can be an individual or group from which BNP-SP samples are taken and a mean BNP-SP level determined Usually, the individual or group will comprise normal healthy individuals or a group of individuals not known to be suffering from ACD, cardiac transplant rejection or ACD/pulmonary disorder. BNP-SP levels in most individuals are between 0-15 pmol/L, and the mean control level is about 10 pmol/L. Alternatively, the control level may be assessed based on a plurality of readings from previously tested individuals or groups. Another example of a control level is a ratiometric measure between BNP-SP and BNP levels in cardiac tissue. The subject's BNP-SP level can be compared to the mean BNP-SP level for that control population. The BNP-SP level in the cardiac control population may be in the order of 1.5 to 3, commonly 2 to 3 or 2.5 to 3 times higher than BNP-SP levels in the normal control population. Alternatively, the control may be one or more readings or the mean of such readings taken from the same subject at an earlier time. Ascertaining appropriate controls and control levels for particular methods is well known in the art.

The term within two hours of onset or clinical presentation includes from 1 minute up to and including 120 minutes from onset of, or presentation at a medical facility with ACD, cardiac transplant rejection or an undiagnosed or suspected ACD/pulmonary disorder. Preferably measurements are made within 1 hour (from 1 minute up to and including 60 minutes) from onset or presentation, preferably within 5 to 45 minutes, preferably 15 to 40 minutes, preferably 20 to 35 minutes, and optimally within 25 to 30 minutes of onset or presentation.

A level "higher" than a control, or a change or deviation from a control is preferably statistically significant. A higher level, deviation from, or change from a control level or mean control level can be considered to exist if the level differs from the control level by 5% or more, by 10% or more, preferably by 20% ore more, more preferably by 50% or more compared to the control level. Statistically significant may alternatively be calculated as $P \leq 0.05$. In a further alternative, higher levels, deviation and changes can be determined by recourse to assay reference limits or reference intervals. These can be calculated from intuitive assessment or non-parametric methods. Overall, these methods calculate the 0.025, and 0.975 fractiles as 0.025*(n+1) and 0.975 (n+1). Such methods are well known in the art.[23,24] Presence of a marker absent in a control, is also contemplated as a higher level, deviation or change.

It will be appreciated that the step of measuring BNP-SP levels in a sample may be a single measurement on a single sample, or repeated measurements on a number of samples. Accordingly, measurement may comprise 1 to 20 measurements of BNP-SP, preferably 1 to 10, preferably 1 to 5, preferably 1 to 3, preferably 1 or 2, preferably 2 or 3 measurements, in samples taken at different times within the first two hours, preferably within one hour of, onset of or clinical presentation. Single, or repeated measurements outside the two hour period may also be taken to establish whether the BNP-SP level has fallen to the normal control level, or cardiac control level.

In one preferred embodiment, the method comprises measuring BNP-SP levels in 1 or 2 samples taken within the first hour of onset or presentation, followed by measuring BNP-SP levels in 1 or 2 samples taken within two to four hours of onset or presentation, or initial measurement of the BNP-SP level, preferably within two to three hours.

As noted above, BNP-SP levels measured within the first two hours of onset or presentation are usually four to ten times higher, commonly five to eight times higher than BNP-SP levels measured in a normal control. As stated above, also included within the ranges are the specific ranges 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, and 9 to 10 times.

In another embodiment, a level of BNP-SP in the sample in the range 20 to 300 pmol/L, preferably 25 to 250 pmol/L, preferably 30 to 180 pmol/L, preferably 35 to 150 pmol/L, preferably 40 to 120 pmol/L, preferably 40 to 90 pmol/L, and preferably 45 to 80 pmol/L is indicative of ACD, cardiac transplant rejection, or distinguishes ACD from a pulmonary disorder.

As stated above, the ranges also include any values within the range such as 20 to 180 pmol/L, 50 to 200 pmol/L, 40 to 130 pmol/L, 50 to 100 pmol/L, 45 to 160 pmol/L, and the like.

The biological sample can be any biological material in which BNP-SP can be located or secreted. This includes any tissue or bodily fluid such as blood, saliva, interstitial fluid, serum, plasma, urine, pericardial fluid and cerebrospinal fluid but is not limited thereto. Preferably the biological sample is a circulatory biological sample, for example blood, serum or plasma. In one embodiment, the biological sample is cardiac tissue.

The presence of the markers and their level of expression in the sample may be determined according to methods known in the art such as Southern Blotting, Northern Blotting, FISH or quantative PCR to quantitate the transcription of mRNA [(Thomas, Pro. NAH, Acad. Sci. USA 77: 5201-5205 1980), (Jain K K, Med Device Technol. 2004 May; 15(4):14-7)], dot blotting, (DNA analysis) or in situ hybridization using an appropriately labelled probe, based on the marker sequences provided herein.

Accordingly, the invention also provides an assay for detecting the presence of a nucleic acid molecule of the invention, in a sample, the method comprising:
(a) contacting the sample with a polynucleotide probe which hybridises to the nucleic acid sequence under stringent hybridisation conditions; and
(b) detecting the presence of a hybridisation complex in the sample.

Preferably the hybridisation probe is a labelled probe. Examples of labels include fluorescent, chemiluminescent, radioenzyme and biotin-avidin labels. Labelling and visualisation of labelled probes is carried out according to known art methods such as those above.

For convenience the nucleic acid probe may be immobilized on a solid support including resins (such as polyacrylamides), carbohydrates (such as sepharose), plastics (such as polycarbonate), and latex beads.

As discussed above the nucleic acid molecule probe may preferably be an RNA, cDNA or DNA molecule. Preferred probes include SEQ ID NOs: 14, 16, 18, 20 and 22.

Stringent hybridisation conditions are as discussed above.

The expression level of the nucleic acid marker may be determined using known art techniques such as RT-PCR and electrophoresis techniques including SDS-PAGE. Using these techniques the DNA or cDNA sequence of a nucleic acid molecule of the invention, in a subject sample is amplified, and the level of DNA or cDNA or RNA measured.

In an alternate method the DNA, cDNA or RNA level may be measured directly in the sample without amplification.

A currently preferred method is Northern blot hybridization analysis. Probes for use in Northern blot hybridization analysis may be prepared based on the marker sequences identified herein. A probe preferably includes at least 12, at least 15, at least 18, at least 24, at least 30, at least 36, preferably at least 42, preferably at least 51, preferably at least 60, preferably at least 70 or more contiguous nucleotides of a reference sequence.

Alternatively, the expression level may be measured using reverse transcription based PCR (RT-PCR) assays using primers specific for the nucleic acid sequences. If desired, comparison of the level of the marker in the sample can be made with reference to a control nucleic acid molecule the expression of which is independent of the parameter or condition being measured. A control nucleic acid molecule refers to a molecule in which the level does not differ between the disorder or transplant rejection state and the healthy state. Levels of the control molecule can be used to normalise levels in the compared populations. An example of such a control molecule is GAP-DH. The markers of the invention will change levels with the disorder.

In one embodiment the measuring step comprises detecting binding between BNP-SP and a binding agent that selectively binds BNP-SP or a fragment or variant thereof. Preferably, the binding agent has low cross-reactivity with other markers of biological events, and more particularly BNP or NT-BNP. The binding agent is preferably an antibody or fragment thereof.

The present invention also relates to such antibodies, or fragments of the antibodies. An antibody that binds to BNP-SP or a fragment or variant thereof may be in any form, including all classes of polyclonal, monoclonal, single chain, human, humanized antibodies and chimeric antibodies produced by genetic recombination. Also included is antiserum obtained by immunizing an animal such as a mouse, rat or rabbit with BNP-SP or a fragment or variant thereof.

A fragment of an antibody or a modified antibody may also be used herein so long as it binds BNP-SP or a fragment or variant thereof. The antibody fragment may be Fab, F(ab'), F(ab'), and Fc or Fv fragment or single chain Fv (scFv), in which Fv fragments from H and L chains are ligated by an appropriate linker (Huston et al. Proc. Natl. Acad. Sci. USA 85:5879-83 (1988)). The "Fc" portion of an antibody refers to that portion of an immunoglobulin heavy chain that comprises one or more heavy chain constant region domains; CH1, CH2 and CH3, but does not include the heavy chain variable region.

Methods for preparing antibodies are well known in the art (see for example Harlow and Lane (1998).[11] Most commonly used antibodies are produced by immunizing a suitable host mammal. Fusion proteins comprising BNP-SP may also be used as immunogens.

An antibody may be modified by conjugation with a variety of molecules, such as polyethylene glycol (PEG). The modified antibody can be obtained by chemically modifying an antibody. These modification methods are conventional in the field.

Alternatively, an antibody may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region. Such antibodies can be prepared using known art methods.

In brief, methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include BNP-SP or a fragment or variant thereof or a fusion protein thereof. It may be useful to conjugate the immunizing agent to a protein known to be immunogenic in the mammal being immunized. Examples of such immunogenic proteins include but are not limited to keyhole limpet hemocyanin, bovine serum albumin, bovine thyroglobulin, and soybean trypsin inhibitor. Examples of adjuvants which may be employed include Freund's complete adjuvant and MPL TDM adjuvant (monophosphoryl Lipid A, synthetic trehalose dicorynomycolate). The immunization protocol may be selected by one skilled in the art without undue experimentation.

Monoclonal antibodies may be prepared using hybridoma methods well known in the art. See for example Kohler and Milstein, 1975[12] and U.S. Pat. No. 4,196,265. The hybridoma cells may be cultured in a suitable culture medium, alternatively, the hybridoma cells may be grown in vivo as ascites in a mammal. Preferred immortalized cell lines are murine myeloma lines, which can be obtained, for example, from the American Type Culture Collection, Virginia, USA Immunoassays may be used to screen for immortalized cell lines which secrete the antibody of interest. Sequences of BNP-SP or fragments or variants thereof may be used in screening.

Accordingly, also contemplated herein are hybridomas which are immortalized cell lines capable of secreting a BNP-SP specific monoclonal antibody.

Well known means for establishing binding specificity of monoclonal antibodies produced by the hybridoma cells include immunoprecipitation, radiolinked immunoassay (RIA), enzyme-linked immunoabsorbent assay (ELISA) and Western blot. (Lutz et al., Exp. Cell. Res. 175:109-124 (1988)). Samples from immunised animals may similarly be screened for the presence of polyclonal antibodies.

To facilitate detection, antibodies and fragments herein may be labelled with detectable markers such as fluorescent, bioluminescent, and chemiluminescent compounds, as well as radioisotopes, magnetic beads and affinity labels (e.g biotin and avidin). Examples of labels which permit indirect measurement of binding include enzymes where the substrate may provide for a coloured fluorescent product, suitable enzymes include horseradish peroxidase, alkaline phosphatase, malate dehydrogenase and the like. Fluorochromes (e.g Texas Red, fluorescein, phycobiliproteins, and phycoerythrin) can be used with a fluorescence activated cell sorter. Labelling techniques are well known in the art.

The monoclonal antibodies secreted by the cells may be isolated or purified from the culture medium or ascites fluid by conventional immunoglobulin purification procedures such as, for example, protein A-Sepharose, hydroxyapatite chromatography, gel electrophoresis, dialysis, or affinity chromatography.

The monoclonal antibodies or fragments may also be produced by recombinant DNA means (see for example U.S. Pat. No. 4,816,567). DNA modifications such as substituting the coding sequence for human heavy and light chain constant domains in place of the homologous murine sequences (U.S. Pat. No. 4,816,567 above) are also possible. The antibodies may be monovalent antibodies. Methods for preparing monovalent antibodies are well known in the art. Production of chimeric bivalent antibodies are also contemplated herein.

The antibodies of the invention may further comprise humanized antibodies or human antibodies. Humanized antibodies include human immunoglobulins in which residues from a complementary determining region (CDR) of the recipient are replaced by residues from a CDR of a non-human species. The production of humanized antibodies from non-human sources such as rabbit, rat and mouse are well known.[13,14,15]

Human antibodies can also be produced using various techniques known in the art, including phage display libraries[16]; and transgenic methods, see, for example Neuberger 1996[17]; and Vaughan et al, 1998[18].

Bispecific antibodies may also be useful. These antibodies are monoclonal, preferably human or humanized, antibodies that have binding specificities for at least two different antigens. For example BNP-SP or a variant or fragment thereof, and an antigen selected from the group including preproBNP, BNP, CK-MB, TnT, TnI, and myoglobin. Antibodies with greater than two specificities for example trispecific antibodies are also contemplated herein.

Methods for making bispecific antibodies are known in the art. See for example Milstein and Cuello 1983[10], Suresh et al., 1986[20] and Brennan et al., 1985[21].

The BNP-SP which is selectively bound by the antibody is BNP-SP or an antigenic variant or fragment thereof as discussed above.

Desirably, the antibody binds the N-terminus or C-terminus of BNP-SP. Examples of specific antigenic peptides which the binding agent selectively binds include BNP-SP(1-10) SEQ ID NO:13, BNP-SP(1-17) SEQ ID NO:15, BNP-SP(12-23) (SEQ ID NO:17), BNP-SP(17-26) SEQ ID NO:19, and BNP-SP(1-26) SEQ ID NO:21.

Binding of BNP-SP can be detected by any means known in the art including specific (antibody based) and non specific (such as HPLC solid phase). Most commonly, antibodies herein are detected using an assay such as ELISA or RIA as noted above. Competitive binding assays, sandwich assays, non-competitive assays, fluoroimmunoassay, immunofluorometric assay, or immunoradiometric assays, luminescence assays, chemiluniescence assays and mass spectrometry analysis such a surface-enhanced laser desorption and ionization (SELDI) electrospray ionization (ESI), matrix assisted laser-desorption ionization (MALDI), fourier transform Ion cyclotron resonance mass spectroscopy (FTICR) alone or in combination with non-specific binding agents such as chromatography formats are also feasible.

Conveniently, an antibody can be fixed to a solid substrate to facilitate washing and isolation of the BNP-SP/antibody complex. Binding of antibodies to a solid support can be achieved using known art techniques. See for example Handbook of Experimental Immunology, 4th edition, Blackwell Scientific Publications, Oxford (1986). Useful solid substrates for antibodies include glass, nylon, paper and plastics. Similarly, BNP-SP can be adsorbed onto a solid substrate such as adsorbent silica, or resin particles, or silicon chips optionally coated or derivatised with ion exchange, reverse phase (eg C18 coating) or other materials. The substrate may be in the form of beads, plates, tubes, sticks or biochips. Biochips or plates with addressable locations and discreet microtitre plates are particularly useful. Also preferred for use are multiplesystems where beads containing antibodies directed to multiple analytes are used to measure levels of the analytes in a single sample. Analytes to be measured may include other cardiac markers as well as BNP-SP or variants or fragments thereof. One example of a suitable multiplex bead system for use herein is the Luminex Fluorokine Multianalyte Profiling system.

Antibody assay methods are well known in the art see for example U.S. Pat. No. 5,221,685, U.S. Pat. No. 5,310,687, U.S. Pat. No. 5,480,792, U.S. Pat. No. 5,525,524, U.S. Pat. No. 5,679,526, U.S. Pat. No. 5,824,799, U.S. Pat. No. 5,851,776, U.S. Pat. No. 5,885,527, U.S. Pat. No. 5,922,615, U.S. Pat. No. 5,939,272, U.S. Pat. No. 5,647,124, U.S. Pat. No. 5,985,579, U.S. Pat. No. 6,019,944, U.S. Pat. No. 6,113,855, U.S. Pat. No. 6,143,576 and for unlabelled assays U.S. Pat. No. 5,955,377, and U.S. Pat. No. 5,631,171 see also Zola, Monoclonal Antibodies: A Manual of Techniques pp 147-158 (CRC Press, Inc 1987), Harlow and Lane (1998) Antibodies, A Laboratory Manual, Cold Spring Harbour Publications, New York, and US 2005/0064511 for a description of assay formats and conditions all of the above references are incorporated herein by reference in their entirety.

Immunoassay analysers are also well known and include Beckman Acess, Abbott AxSym, Roche ElecSys and Dade Behring Status systems amongst others which are well described[22].

Binding of BNP-SP and an antibody to form a complex can be detected directly or indirectly. Direct detection is carried out using labels such as fluorescence, luminescence, radionuclides, metals, dyes and the like. Indirect detection includes binding detectable labels such as digoxin or enzymes such as horseradish peroxidase and alkaline phosphatase to form a labelled BNP-SP antibody followed by a step of detecting the label by addition of detection reagents.

Horseradish peroxidase for example can be incubated with substrates such as o-Phenylenediamine Dihyhydrochloride (OPD) and peroxide to generate a coloured product whose absorbance can be measured, or with luminol and peroxide to give chemiluminescent light which can be measured in a luminometer as is known in the art. Biotin or digoxin can be reacted with binding agents that bind strongly to them. For example, the proteins avidin and streptavidin will bind strongly to biotin. A further measurable label is then covalently bound or linked thereto either by direct reaction with the protein, or through the use of commonly available crosslinking agents such as MCS and carbodiimide, or by addition of chelating agents.

Generally, the complex is separated from the uncomplexed reagents for example by centrifugation. If the antibody is labelled, the amount of complex will be reflected by the amount of label detected. Alternatively, a BNP-SP may be labelled by binding to an antibody and detected in a competitive assay by measuring a reduction in bound labelled BNP-SP when the antibody-labelled-BNP-SP is incubated with a biological sample containing unlabelled BNP-SP. Other immunoassays may be used for example a sandwich assay.

In one example, following contact with the antibody, usually overnight for 18 to 25 hours at 4° C., or for 1 to 2 to 4 hours at 25° C. to 40° C., the labelled BNP-SP bound to the binding agent (antibody) is separated from the unbound labelled BNP-SP. In solution phase assays, the separation may be accomplished by addition of an anti gamma globulin antibody (second-antibody) coupled to solid phase particles such as cellulose, or magnetic material. The second-antibody is raised in a different species to that used for the primary antibody and binds the primary antibody. All primary antibodies are therefore bound to the solid phase via the second antibody. This complex is removed from solution by centrifugation or magnetic attraction and the bound labelled peptide measured using the label bound to it. Other options for separating bound from free label include formation of immune complexes, which precipitate from solution, precipitation of the antibodies by polyethyleneglycol or binding free labelled peptide to charcoal and removal from solution by centrifugation of filtration. The label in the separated bound or free phase is measured by an appropriate method such as those presented above.

Competitive binding assays can also be configured as solid phase assays that are easier to perform and are therefore preferable to those above. This type of assay uses plates with wells (commonly known as ELISA or immunoassay plates), solid beads or the surfaces of tubes. The primary antibody is either adsorbed or covalently bound to the surface of the plate, bead or tube, or is bound indirectly through a second anti gamma globulin or anti Fc region antibody adsorbed or covalently bound to the plate. Sample and labelled peptide (as above) are added to the plate either together or sequentially and incubated under conditions allowing competition for antibody binding between BNP-SP in the sample and the labelled peptide. Unbound labelled peptide can subsequently be aspirated off and the plate rinsed leaving the antibody bound labelled peptide attached to the plate. The labelled peptide can then be measured using techniques described above.

Sandwich type assays are more preferred for reasons of specificity, speed and greater measuring range. In this type of assay an excess of the primary antibody to BNP-SP is attached to the well of an ELISA plate, bead or tube via adsorption, covalent coupling, or an anti Fc or gamma globulin antibody, as described above for solid phase competition binding assays. Sample fluid or extract is contacted with the antibody attached to the solid phase. Because the antibody is in excess this binding reaction is usually rapid. A second antibody to BNP-SP is also incubated with the sample either simultaneously or sequentially with the primary antibody. This second antibody is chosen to bind to a site on BNP-SP that is different from the binding site of the primary antibody. These two antibody reactions result in a sandwich with the BNP-SP from the sample sandwiched between the two antibodies. The second antibody is usually labelled with a readily measurable compound as detailed above for competitive binding assays. Alternatively a labelled third antibody which binds specifically to the second antibody may be contacted with the sample. After washing away the unbound material the bound labelled antibody can be measured and quantified by methods outlined for competitive binding assays.

A dipstick type assay may also be used. These assays are well known in the art. They may for example, employ small particles such as gold or coloured latex particles with specific antibodies attached. The liquid sample to be measured may be added to one end of a membrane or paper strip preloaded with the particles and allowed to migrate along the strip. Binding of the antigen in the sample to the particles modifies the ability of the particles to bind to trapping sites, which contain binding agents for the particles such as antigens or antibodies, further along the strip. Accumulation of the coloured particles at these sites results in colour development are dependent on the concentration of competing antigen in the sample. Other dipstick methods may employ antibodies covalently bound to paper or membrane strips to trap antigen in the sample. Subsequent reactions employing second antibodies coupled to enzymes such as horse radish peroxidase and incubation with substrates to produce colour, fluorescent or chemiluminescent light output will enable quantitation of antigen in the sample.

As discussed in the following examples, radioimmunoassay (RIA) is a currently preferred laboratory technique. In one RIA a radiolabelled antigen and unlabelled antigen are employed in competitive binding with an antibody. Common radiolabels include $^{125}$I, $^{131}$I, $^{3}$H and $^{14}$C.

Radioimmunoassays involving precipitation of BNP-SP with a specific antibody and radiolabelled antibody binding protein can measure the amount of labelled antibody in the precipitate as proportional to the amount of BNP-SP in the sample. Alternatively, a labelled BNP-SP is produced and an unlabelled antibody binding protein is used. A biological sample to be tested is then added. The decrease in counts from the labelled BNP-SP is proportional to the amount of BNP-SP in the sample.

In RIA it is also feasible to separate bound BNP-SP from free BNP-SP. This may involve precipitating the BNP-SP/antibody complex with a second antibody. For example, if the BNP-SP antibody complex contains rabbit antibody then donkey anti-rabbit antibody can be used to precipitate the complex and the amount of label counted. For example in an LKB, Gammamaster counter. See Hunt et al.[22]

The methods of the invention further comprise measuring the levels of one or more non-BNP-SP markers of the ACD, cardiac transplant rejection, or ACD/pulmonary disorder. The level of the other marker or markers can be compared to mean control levels from a control population. A deviation in the measured level from the mean control level is predictive or diagnostic of ACD or cardiac transplant rejection.

While the methods of the invention have been described with respect to a higher level or increase in BNP-SP levels being indicative of ACD, or cardiac transplant rejection, it is also possible that in some events or disorders the levels of BNP-SP will fall. Measuring deviations below a control level are also contemplated.

Other markers which are particularly useful herein include troponin T, troponin I, creatin kinase MB, myoglobin, BNP, NT-BNP LDH, aspartate aminotransferase, H-FABP, endothelin, adrenomedullin, rennin and angiotensin II[1]. These markers are all implicated in cardiac dysfunction or disease. Correlating the level of BNP-SP with other markers can increase the predictive, diagnostic or monitoring value of BNP-SP. In the case of ACD, cardiac transplant rejection or ACD/pulmonary disorder combining BNP-SP marker levels with known cardiac markers can increase the predictive or diagnostic value of a patient outcome.

Analysis of a number of peptide markers can be carried out simultaneously or separately using a single test sample. Simultaneous, two or multi-site format assays are preferred. Multiplex bead, microassay or biochip systems are particularly useful. The beads, assays or chips can have a number of discreet, often addressable locations, comprising an antibody to one or more markers including BNP-SP. The one or more markers include more than one BNP-SP marker. For example, it may be useful to assay for N-terminal and C-terminal BNP-SP fragments and combine the assay results. Many other such marker combinations are feasible. US2005/0064511 provides a description of chips and techniques useful in the present invention. Luminex provides a multiplex bead system useful in the present invention.

Where a subject is to be monitored, a number of biological samples may be taken over time. Serial sampling allows changes in marker levels, particular BNP-SP to be measured over time. Sampling can provide information on the approximate onset time of an event, the severity of the event, which therapeutic regimes may be appropriate, response to therapeutic regimes employed, and long term prognosis. Analysis may be carried out at points of care such as in ambulances, doctors offices, on clinical presentation, during hospital stays, in outpatients, or during routine health screening.

The methods of the invention may also be performed in conjunction with an analysis of one or more risk factors such as but not limited to age, weight, sex and family history of events such as cardiac events. Test results can also be used in conjunction with the methods of the invention. For example, ECG results and clinical examination. A statistically significant increase in circulating level of BNP-SP, together with one or more additional risk factors or test results may be used to more accurately diagnose or prognose the subject's condition.

The methods herein can also be used as a guide to therapy. For example what therapies to initiate and when, therapy monitoring, detection of positive or adverse effects of therapy, for example heart toxicity of antimitotic drugs, and adjustment of therapeutic regimes if and when required dependent on results. This can improve short, medium and long term outcomes for patients. For a guide to treatments see Troughton et al.[8]

Acute Cardiac Disorders

The applicants have shown that concentrations of the full-length BNP-SP molecule (1-26) and various fragments thereof are correlated with acute cardiac disorders. Moreover, BNP-SP levels are at their highest upon clinical presentation in the case of patients presenting with suspected acute myocardial infarction (AMI). Patients presenting with acute cardiac disorders, and in particular acute cardiac ischemia may or may not experience subsequent myocardial infarction (MI). The group which does not experience MI can not be readily diagnosed using current clinical techniques and markers. For the first time, the applicants have therefore provided a useful early and specific marker for myocardial damage associated with MI. This may allow the early diagnosis of myocardial damage due to adverse events (AEs) and allow a physician to distinguish such cases from other acute coronary syndromes as well as from other causes of a chest pain. For example angina, gastro-intestinal disease, lung/pleural disorders and the like. This significantly shortens the window of 6 hours to 12 hours currently experienced waiting for elevation of levels of current cardiac biomarkers such as myoglobin, CK-MB, TnT and TnI. A more precise diagnosis and treatment can therefore be effected earlier, reducing morbidity and mortality and giving better prognostic outcomes.

The invention has particular application in monitoring reperfusion treatment in cardiac patients. Reperfusion treatment commonly includes percutaneous coronary intervention (eg angioplasty) and/or pharmacological treatment. Thrombolytic drugs for revascularisation are commonly employed in pharmacological treatment. Adjunctive therapies include anticoagulant and anti-platelet therapies. Reperfusion treatment is most effective when employed as soon as possible after diagnosis. BNP-SP testing to accelerate diagnosis allows prompt introduction of reperfusion treatment. Effectiveness of treatment can also be monitored by repeat testing, and therapy adjusted as appropriate. For a comprehensive discussion of reperfusion treatment see Braunwald et al herein[1].

Cardiac Disease

The methods of the invention can also be used to diagnose or predict cardiac disease in a subject.

The applicants have shown that in patients with acute cardiac disorders the levels of BNP-SP remain elevated for at least 6 weeks after a cardiac event. It is similarly predictable that patients with cardiac disease or at risk of same will exhibit a higher level of BNP-SP than mean control levels in a control population. Unlike BNP, the applicants have shown that levels of BNP-SP are not affected by the age of the population. This suggests BNP-SP has broad applications as a marker of cardiac disease.

Cardiac Transplant Rejection

The invention also has applications in monitoring heart transplant, commonly a cardiac allograft transplant, rejection through regular tissue biopsy during and after transplant using BNP-SP measurements. An increase in BNP-SP levels measured within two hours of heart transplant relative to a control level may be predictive or diagnostic of a rejection episode.

The present invention also provides an assay for BNP-SP in a biological sample obtained from a subject within two hours from onset of, or within two hours of clinical presentation with ACD, cardiac transplant rejection or ACD/pulmonary disorder, the assay comprising detecting and measuring the level of BNP-SP in the sample using any known methods. Preferably, the assay is an in vitro assay. Such methods include all of the known assay techniques discussed above as well as gel electrophoresis techniques, Western blot, gas phase spectroscopy, atomic force microscopy, surface plasmon resonance, mass spectroscopy but not limited thereto[23].

In one embodiment the assay comprises one or more nucleic acid sequences which bind to one or more of the BNP-SP nucleic acid sequences of the invention. A large range of sense and antisense probes and primers can be designed from the nucleic acid sequences herein. The expression level of the BNP-SP sequence is identified using known art techniques discussed above. The array can be a solid substrate e.g., a "chip" as described in U.S. Pat. No. 5,744,305 or a nitrocellulose membrane.

Proteins expressed by the BNP-SP marker herein may also be used in assays, and results compared to expression levels of the same protein expressed in a normal control sample. Protein presence and quantity may be assessed using assay formats known in the art and discussed herein.

The presence of BNP-SP is preferably detected in the sample by binding BNP-SP to a binding agent such as an antibody of the invention and measuring the presence of the amount of bound BNP-SP.

As noted above, antibodies selective for BNP-SP including variants and fragments thereof form a further aspect of the invention and the antibodies may be prepared by the techniques discussed above. The antibodies are useful in the methods and assay of the invention.

In a further aspect, the invention provides a kit for predicting, diagnosing or monitoring acute cardiac disorder (ACD), cardiac transplant rejection, or ACD/pulmonary disorder, comprising a BNP-SP binding agent of the invention, wherein the kit is for use with a biological sample obtained from a subject within two hours of onset of, or clinical presentation with ACD, cardiac transplant rejection, or ACD/pulmonary disorder.

The invention also provides a kit for predicting, diagnosing or monitoring an acute cardiac disorder (ACD), cardiac transplant rejection, or an ACD/pulmonary disorder comprising a binding agent of the invention, wherein the kit is calibrated to measure BNP-SP levels in the range of 0.1 to 500 pmol/L, preferably 1 to 400 pmol/L, preferably 10 to 350 pmol/L, preferably 20 to 300 pmol/L, preferably 25 to 250 pmol/L, preferably 30 to 180 pmol/L, preferably 35 to 150 pmol/L, preferably 40 to 120 pmol/L.

Calibration of assays can be effected according to known art techniques, for example using blood samples with known levels of BNP-SP, or a set of calibrates with different known levels of BNP-SP in each. Test strips for use in diagnostic kits are commonly calibrated during manufacture. See for example U.S. Pat. No. 6,780,645. The kit is useful for measuring the level of BNP-SP in a biological sample. The detection reagents may be oligonucleotide sequences complementary to BNP-SP or a fragment of the BNP-SP marker, or antibodies which bind to the polypeptides encoded by the marker. The reagents may be bound to a solid matrix as discussed above or packaged with reagents for binding them to the matrix. The solid matrix or substrate may be in the form of beads, plates, tubes, dip sticks, strips or biochips all as discussed above.

Detection reagents include wash reagents and reagents capable of detecting bound antibodies (such as labelled secondary antibodies), or reagents capable of reacting with the labelled antibody.

The kit will also conveniently include a control reagent (positive and/or negative) and/or a means for detecting the nucleic acid or antibody. Instructions for use may also be included with the kit, such as taking a biological sample from a subject within two hours of onset or presentation with ACD, cardiac transplant rejection or ACD/pulmonary disorder, measuring the level of BNP-SP in the sample, comparing same to a control level and associating the result with cardiac status. Generally an increase in the BNP-SP marker level from a control is indicative of ACD or cardiac transplant rejection, or ACD as opposed to a pulmonary disorder.

Most usually, the kits will be formatted for assays known in the art, and more usually for PCR, Northern hybridization or Southern ELISA assays, as are known in the art.

The kits may also include one or more additional markers for ACD, transplant rejection, or ACD/pulmonary disorders. In the case of ACS the additional marker may include one or more of troponin T, troponin I, creatin kinase MB, myoglobin, BNP, NT-BNP, LDH, aspartate aminotransferase, H-FABP, endothelin, adrenomedullin, rennin and ongrotensin II. In one embodiment all of the markers are included in the kit.

The kit will be comprised of one or more containers and may also include collection equipment, for example, bottles, bags (such as intravenous fluids bags), vials, syringes, and test tubes. At least one container holds a product which is effective for predicting, diagnosing, or monitoring ACD (particularly ACS), transplant rejection, or ACD/pulmonary disorder. The product is usually a nucleic acid molecule, polypeptide or a binding agent of the invention, or a composition comprising any of these. In a preferred embodiment, an instruction or label on, or associated with, the container indicates that the composition is used for predicting, diagnosing, or monitoring ACD (particularly ACS), transplant rejection, or ACD/pulmonary disorders. Other components may include needles, diluents and buffers. Usefully, the kit may include at least one container comprising a pharmaceutically-acceptable buffer, such as phosphate-buffered saline, Ringer's solution and dextrose solution.

Binding agents that selectively bind BNP-SP are desirably included in the kit. Preferably, the binding agent is an antibody. The antibody used in the assays and kits may be monoclonal or polyclonal and may be prepared in any mammal as discussed above. The antibodies are preferably prepared against a native peptide encoded or indicated by a BNP-SP nucleic acid sequence of the invention, BNP-SP (1-26), or a synthetic peptide based on same, or may be raised against an exogenous sequence fused to a nucleic acid sequence encoding a BNP-SP peptide of the invention.

In one kit embodiment a BNP-SP detection reagent is immobilized on a solid matrix such as a porous strip to form at least one BNP-SP detection site. The measurement or detection region of the porous strip may include a plurality of detection sites, such detection sites containing a BNP-SP detection reagent. The sites may be arranged in a bar, cross or dot or other arrangement. A test strip may also contain sites for negative and/or positive controls. The control sites may alternatively be on a different strip. The different detection sites may contain different amounts of immobilized nucleic acids or antibodies eg, a higher amount in the first detection site and lower amounts in subsequent sites. Upon the addition of a test biological sample the number of sites displaying a detectable signal provides a quantitative indication of the amount of BNP-SP present in the sample.

Also included in the kit may be a device for sample analysis comprising a disposable testing cartridge with appropriate components (markers, antibodies and reagents) to carry out sample testing. The device will conveniently include a testing zone and test result window. Immunochromatographic cartridges are examples of such devices. See for example U.S. Pat. No. 6,399,398; U.S. Pat. No. 6,235,241 and U.S. Pat. No. 5,504,013.

Alternatively, the device may be an electronic device which allows input, storage and evaluation of levels of the measured marker against control levels and other marker levels. US 2006/0234315 provides examples of such devices.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents; or such sources of information, in any jurisdiction, are prior art, or form part of the common general knowledge in the art.

The invention will now be illustrated in a non-limiting way be reference to the following examples.

EXAMPLE 1

Methods

All human protocols were approved by the Upper South Regional Ethics Committee of the Ministry of Health, New Zealand and were performed in accord with the Declaration of Helsinki.

Chemicals

Synthetic human BNP signal peptides BNP-SP (1-10), BNP-SP(17-26) and BNP-SP(1-26) (SEQ ID NO:1) were synthesised by Mimotopes (Australia). All buffer reagents were purchased from BDH and/or Sigma. BNP-SP (17-26) was synthesised with the C-terminal extended with cysteine for directional carrier coupling. BNP-SP (17-26) was also C-terminally extended with a tyrosyl residue for tracer preparation on the same peptide.

Human Studies

For the healthy volunteer reference range study, blood samples were obtained from 13 healthy volunteers (6 woman, average age 43±12 years (range 22-60 years), BMI 24.4±3.9 kg/m$^2$) after an overnight fast.

For analysis of BNP-SP concentrations in acute cardiac injury, we studied 10 consecutive patients (4 woman, average age 70±8 years (range 59-79 years)), presenting to the Coronary Care Unit at Christchurch Hospital within 6 h of the onset of chest pain and clear evidence of ST-elevation acute MI, together with a rise then fall in plasma troponin T (TnT). Patients with cardiogenic shock were excluded. Five patients had previously documented hyperlipidaemia, four had hypertension, one had an earlier MI, one was being treated for cardiac failure and two had diabetes mellitus. Medications on admission were diuretics (two patients), angiotensin-converting enzyme inhibitors (two patients), aspirin (seven patients), β-blockers (two patients). One patient had primary percutaneous transluminal coronary angioplasty (PTCA for anterior MI), nine patients received thrombolysis. Seven patients had an ECG during the hospital stay. Across all patients, the average ejection fraction was 54% (range, 24-75%). Average hospital stay was 6.6 days (range, 3-15 days). The time between the onset of chest pain and drawing of the baseline (time 0) venous sample was 3.9±0.3 h. An 18-gauge intravenous cannula was inserted into a forearm vein for blood sampling. Venous samples (10 ml) were drawn on admission to the Coronary Care Unit (time 0) and thereafter at 0.5, 1, 4, 8, 12, 24 and 72 h as in-patients, and at 1, 6 and 12 weeks as out-patients. Samples were taken into tubes on ice and centrifuged at +4° C. at 2700 g for 5 min and the plasma stored at −80° C. until analysed.

Plasma Extraction

All plasma samples were extracted on SepPak manufacturer waters, USA cartridges as previously described[22], dried and stored at −20° C. prior to RIA and HPLC.

Hormone Concentration Analysis

Plasma samples were assayed for TnT, CK-MB and myoglobin using heterogeneous immunoassays on an Elecsys 2010 using ruthenium-labelled biotinylated antibodies according to standard manufacturers' protocols, Roche Diagnostics.[18] Immunoreactive (IR) BNP and N-BNP concentrations were measured using our previously described assays.[6-8] BNP-SP was measured by specific RIA as follows:

BNP-SP RIA

For the measurement of putative human BNP-SP IR peptides, we generated a novel and specific RIA directed against amino acids 17-26 of the human preproBNP(1-26) signal sequence (SEQ ID NO:1)

Antibody Generation preproBNPCys[25] (17-26) was coupled to malemide treated N-e-maleimidocaproyloxy succinimide ester (EMCS) derivatised BSA in PBS (pH 7.0) by gentle mixing at room temperature. Coupled peptide was emulsified with Freund's adjuvant and injected subcutaneously in 2 New Zealand white rabbits over 4-5 sites at monthly intervals. Rabbits were bled 12 days after injection to assess antibody titres until adequate levels were achieved. For RIA, BNP-SP IR was determined using antiserum at a final dilution of 1:6,000. This antiserum has no detectable cross reactivity with human proBNP(1-13), proBNP(1-76), proANP(1-30), ANP, BNP, endothelin 1, Angiotensin II, Angiotensin(1-7), urotensin II, CNP, proCNP (1-15), adrenomedullin, urocortin I and urocortin II (all <0.01%).

Iodination and Assay Method preproBNP Tyr[25] (17-26) was iodinated via the Chloramine T method and purified on reverse phase HPLC as previously described[22] All samples, standards, radioactive traces and antiserum solutions were diluted in potassium based assay buffer.[22] The assay incubate consisted of 100 μL sample or standard (0-640 pmol human preproBNP(17-26) combined with 100 μL antiserum which was vortexed and incubated at 4° C. for 24 hours. 100 μL of trace (4000-5000 cpm) was then added and further incubated for 24 hours at 4° C. Free and bound immunoreactivities were finally separated by solid phase second antibody method (donkey anti-rabbit Sac-Cel) and counted in a Gammamaster counter (LKB, Uppsala, Sweden).

High Performance Liquid Chromatography (HPLC)

Plasma extracts were subjected to size-exclusion HPLC (SE-HPLC) at room temperature on a TSK-Gel G2000SW peptide column (Toyosoda, Tokyo, Japan) using isocratic conditions of 60% acetonitrile/0.1% trifluoroacetic acid (TFA) at a flow rate of 0.25/ml/minute. Fractions were collected at 1 minute intervals and subjected to BNP-SP RIA. The SE-HPLC column was calibrated using dextran blue (Vo), cytochrome C (~Mr 12,400), rat BNP45 (~Mr 5,000), angiotensin II (~Mr 1,045) and glycine (Vt). BNP-SP IR identified by SE-HPLC/RIA were then further characterised on a Brownlee $C_{18}$ reverse phase HPLC (RP-HPLC) column (Applied Biosystems, CA) with a linear eluting gradient from 12%-48% acetonitrile/0.1% TFA over 40 minutes, at a flow rate 1 ml/minute. One minute fractions were collected, dried under an air stream and subjected to specific RIA as for SE-HPLC. RP-HPLC was calibrated using synthetic preproBNP(17-26).

Statistical Analysis

All results are presented as mean±SEM. Time-course data were analysed using two-way ANOVA for repeated measurements followed by least significant difference post-hoc testing. Correlation analysis of plasma hormone concentrations was carried out using a general linear regression model. In all analyses, a P-value<0.05 was considered significant.

Results

Figure 4:
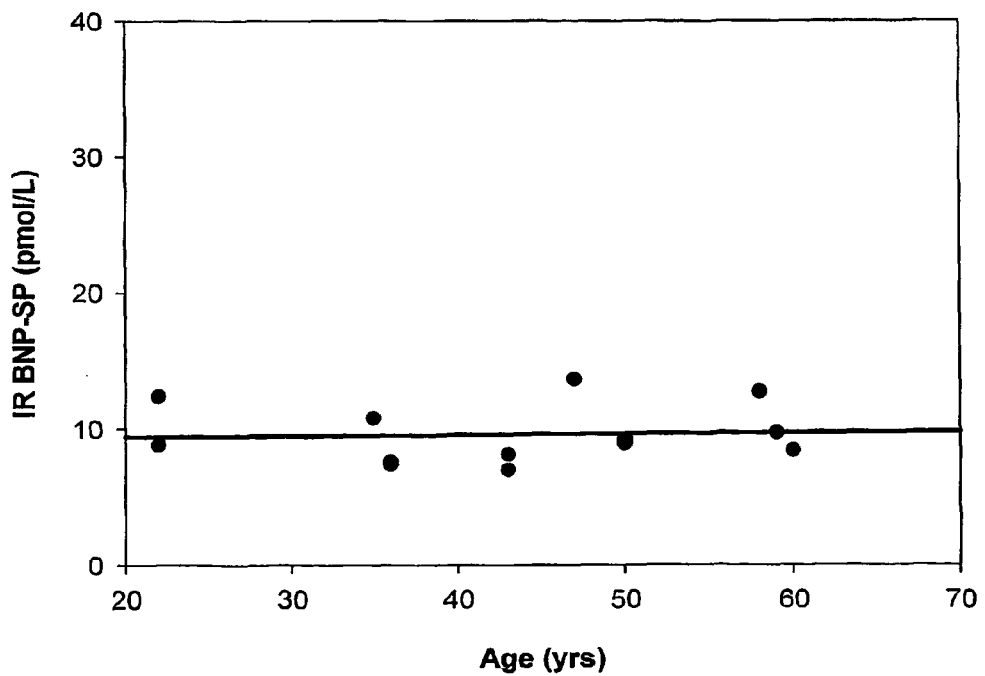
FIG. 4 shows the results of a radioimmunoassay demonstrating that plasma concentrations of BNP-SP in healthy humans do not show any correlation with age.
Figure 5:
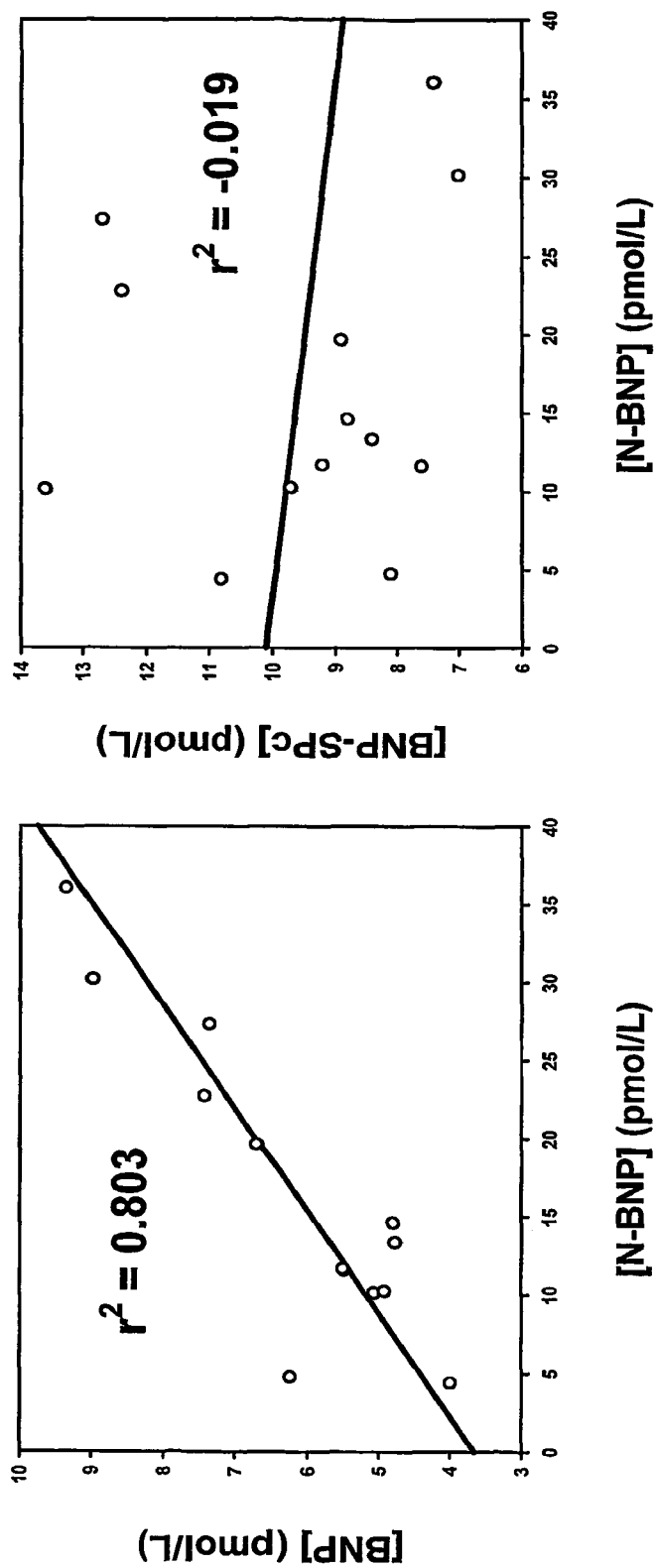
FIG. 5 shows the results of a radioimmunoassay demonstrating that plasma levels of BNP and N-BNP in normal healthy humans (n=13) show close correlation (left panel) whereas BNP-SP concentrations do not correlate with N-BNP (right panel)

To determine if the 26 amino acid SP of BNP, or fragments derived from it, are present in circulation of humans, we developed a specific radioimmunoassay (RIA) directed against residues 17-26 of preproBNP(1-26) (BNP-SP, FIG. 2). Dilution of plasma extracts demonstrate parallelism with the standard curve (FIG. 3) and plasma concentrations of BNP-SP in healthy humans were 9.6±2.2 pmol/L (n=13). In healthy humans, concentrations of BNP-SP IR in blood do not show a significant correlation with age (FIG. 4). However, while plasma BNP-SP levels are similar to those of its sibling peptides BNP and N-BNP, they do not correlate with either peptide (FIG. 5).

Figure 6:
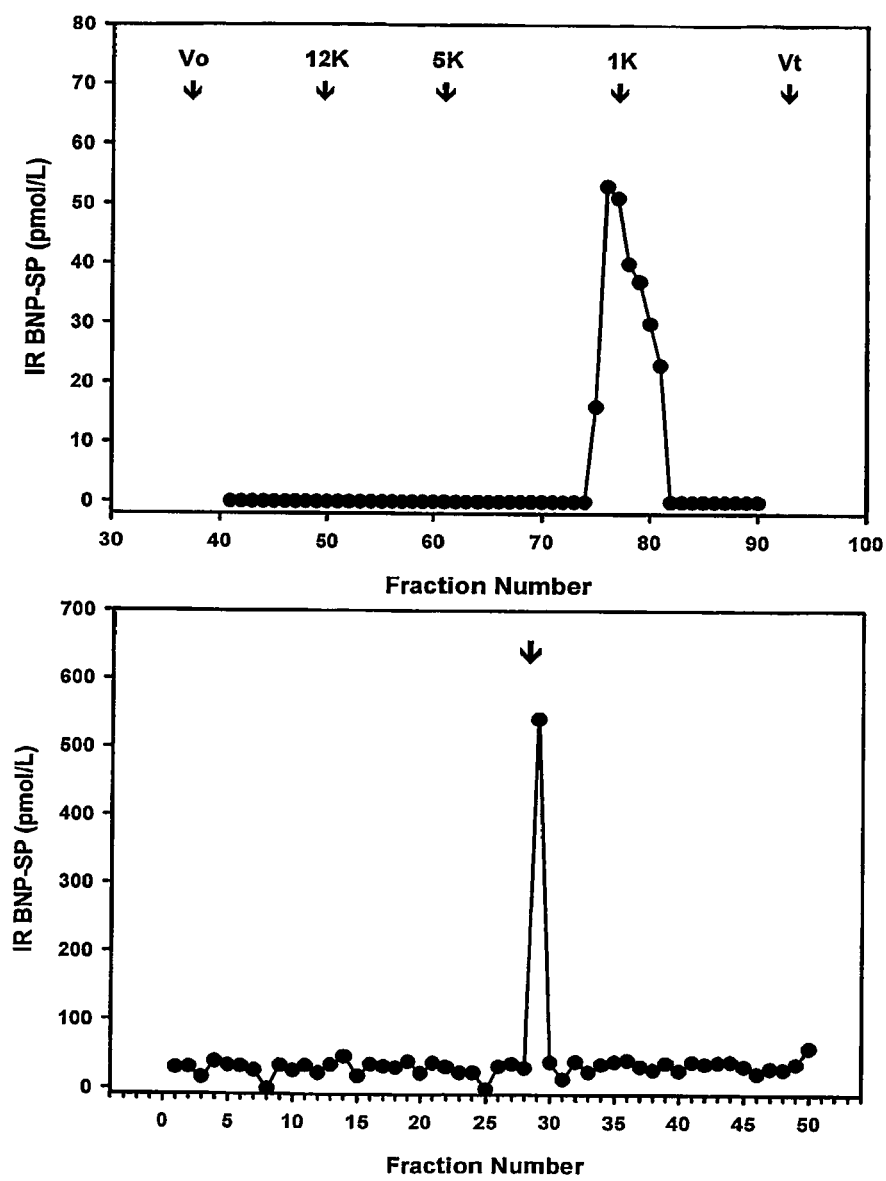
FIG. 6 shows the results of a radioimmunoassay SEHPLC (top panel) and RPHPLC bottom panel) analysis of BNP-SP in human plasma which suggests BNP-SP elutes close to synthetic BNP-SP (downward arrow, bottom panel)

Biochemical analysis of IR plasma BNP-SP by reverse phase (RP) and size exclusion (SE) high performance liquid chromatography (HPLC) suggest that our specific RIA detects fragment(s) of BNP-SP that elute with an approximate Mr 1,000-2,000 on SE-HPLC and close to the elution time of synthetic BNP-SP on RP-HPLC (FIG. 6).

Figure 7:
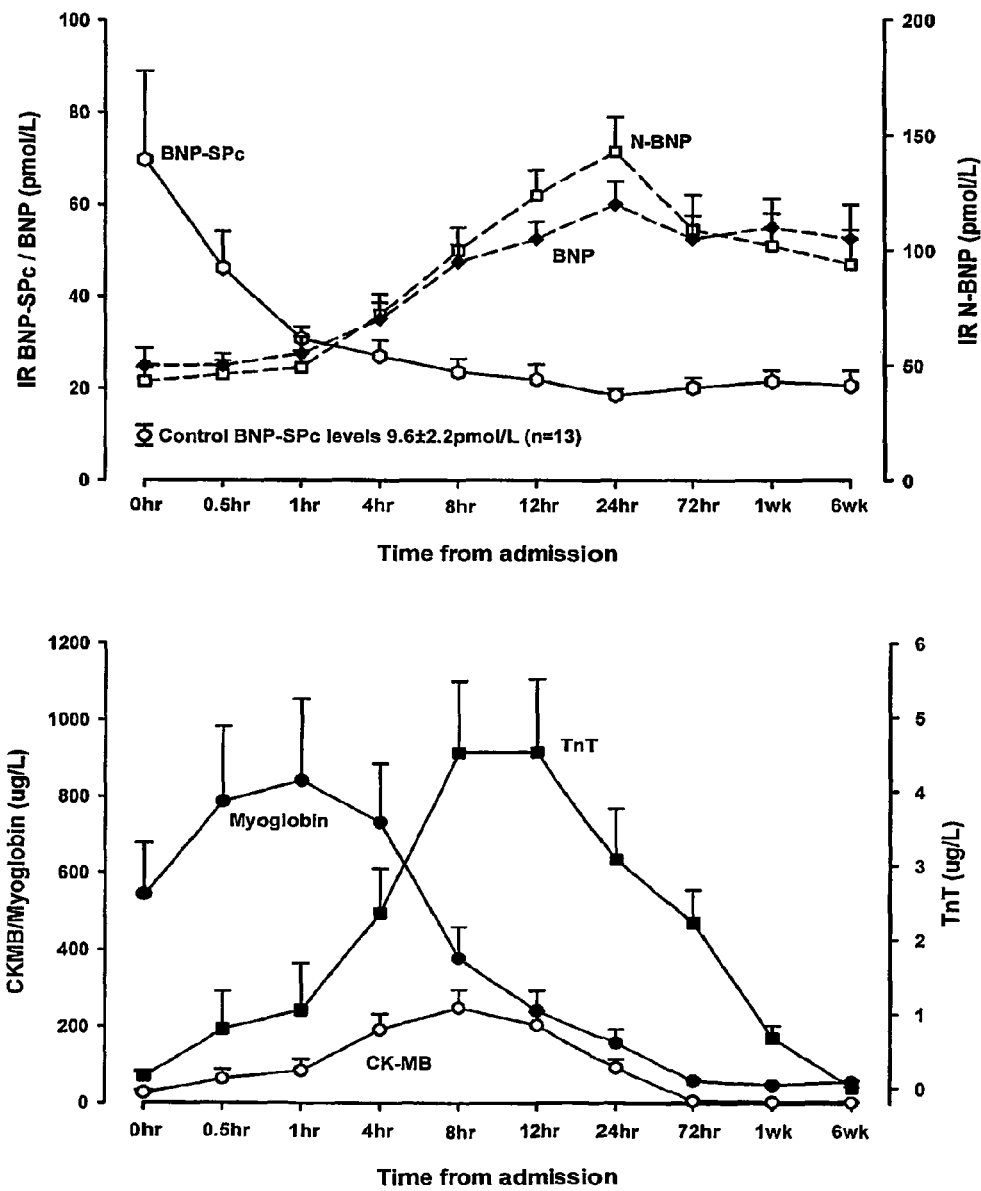
FIG. 7. Radioimmunoassay results showing Upper panel: Concentrations of BNP-SP (open hexagon), BNP (filled circles) and N-BNP (open squares) in plasma drawn from AMI patients (n=10) at the times shown from hospital admission. In contrast with BNP and N-BNP levels which peaked at 24 hours post-admission, highest levels of BNP-SP were seen at admission, being some 7-fold higher on average than levels measured in normal healthy individuals (open circle). Lower panel: matched, time course concentration profiles of CK-MB, myoglobin and TnT in the same patients in upper panel.

Having established that IR BNP-SP peptides are present in human plasma we then measured serial concentrations of IR BNP-SP in patients with documented AMI (n=10, FIG. 7). Highest concentrations of IR BNP-SP were observed at hospital admission and slowly dropped to stable levels over 6 weeks Importantly, average peak levels at admission were 7-fold higher (range 4-12) than levels in normal healthy volunteers and remained 3-fold higher up to 6 weeks. This pattern stands in contrast to that of BNP and N-BNP whose peaks levels do not occur until 24 hours post-admission (FIG. 7). Peak concentrations of myoglobin occurred 1-2 hours after hospital admission, whereas peak TnT and CK-MB levels were not attained until 8-12 hours after admission.

EXAMPLE 2

Figure 9:
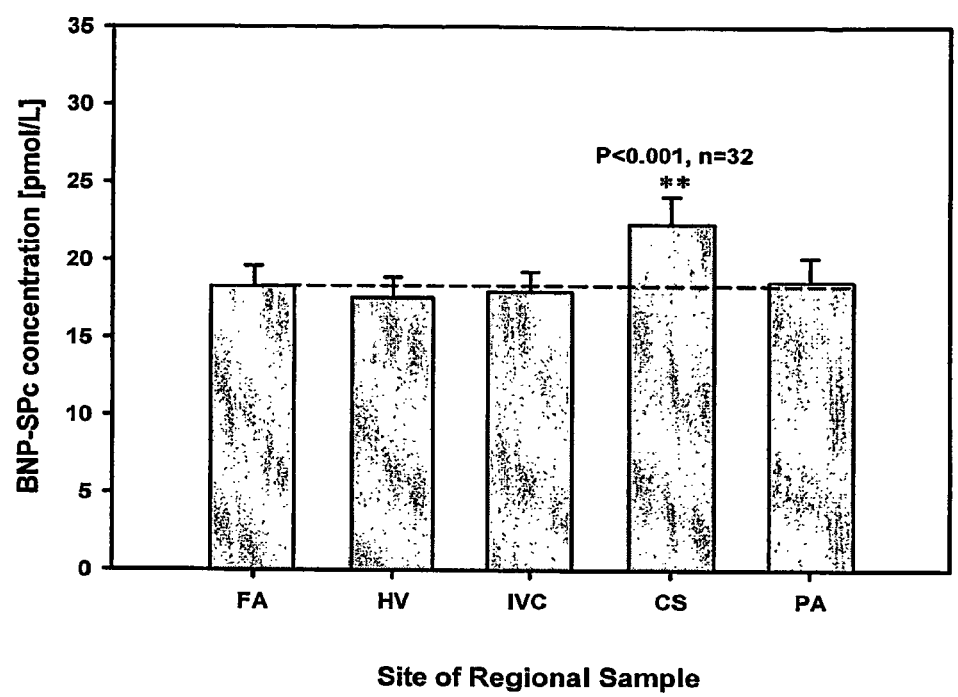
FIG. 9. Is a bar graph showing circulating BNP-SP concentrations in patients are derived from a cardiac source.

Thirty two patients with clinically stable suspected ACS were catheterized and blood samples from multiple organ sites: these were the femoral artery (FA), hepatic vein (HV, inferior vena cava (IVC), cardiac coronary sinus vein (CS) and pulmonary artery (PA). Blood was collected into chilled EDTA tubes, prepared from plasma by centrifugation and the plasma submitted to BNP-SP RIA. FIG. 9 clearly shows that the highest site of BNP-SP concentration is the CS, the vein draining the heart, especially the ventricles. This is strong evidence that the heart is the predominant site of BNP-SP secretion and is consistent with the known gene expression pattern of BNP, being highest in the heart.

CONCLUSION

Circulating BNP-SP concentrations in clinically stable patients are derived from cardiac sources. The significant cardiac secretion, is consistent with BNP-SP being a cardiac hormone.

DISCUSSION

This evidence is the first to document the signal peptide of preproBNP as being present in the circulation and extracellular space within two hours of a patient presenting with ACD or within two hours of the onset of ACD. We show in the first instance that the measurement of BNP-SP in blood has potential as a rapid biomarker of acute cardiac ischemia and/or subsequent injury and in the second instance, that measurement of BNP-SP after the event has potential merit as a marker of long term prognosis and outcome.

Those skilled in the art will of course appreciate that the above description is provided by way of example and that the invention is not limited thereto.

REFERENCES

1. Braunwald E, Zipes D P, Libby P. Acute myocardial infarction Chp. 35 Heart disease: a textbook of cardiovascular medicine, $6^{th}$ ed. 2001. pgs. 1114-1231.
2. Richards A M, Nicholls M G, Yandle T G, Frampton C, Espiner E A, Turner J G, Buttimore R C, Lainchbury J G, Elliott J M, Ikram H, Crozier I G, Smyth D W. Plasma N-terminal pro-brain natriuretic peptide and adrenomedullin: new neurohormonal predictors of left ventricular function and prognosis after myocardial infarction. Circulation 1998 97:1921-1929.
3. Jernberg T, Stridsberg M, Venge P, Lindahl B. N-terminal pro Brain Natriuretic Peptide on admission for early risk stratification of patients with chest pain and no ST-segment elevation. J. Am. Coll. Cardiology 2002 40:437-445.
4. Omland T, Persson A, Ng L, O'Brien R, Karlsson T, Herlitz J, Hartford M, Caidahl K. N-terminal pro-B-type natriuretic peptide and long-term mortality in acute coronary syndromes. Circulation. 2002 106:2913-2918.
5. Pemberton C J, Johnson M L, Yandle T G, Espiner E A. Deconvolution Analysis of the Secretion and Elimination of Cardiac Natriuretic Peptides During Acute Volume Overload. Hypertension 2000; 36: 355-359.
6. Richards A M, Nicholls M G, Troughton R W, Lainchbury J G, Elliott J, Frampton C, Espiner E A, Crozier I G, Yandle T G, Turner J. Antecedent hypertension and heart failure after myocardial infarction. J. Am. Coll. Cardiology. 2002 39: 1182-1188.
7. Troughton R W, Prior D L, Pereira J J, Martin M, Fogarty A, Morehead A, Yandle T G, Richards A M, Starling R C, Young J B, Thomas J D, Klein A L. Plasma B-type natriuretic peptide levels in systolic heart failure: importance of left ventricular diastolic function and right ventricular systolic function. J Am Coll Cardiol. 2004 43:416-422.
8. Troughton R W, Frampton C M, Yandle T G, Espiner E A, Nicholls M G, Richards A M. Treatment of heart failure guided by plasma amino-terminal brain natriuretic peptide (N-BNP) concentrations. Lancet 2000 355: 1126.1130.
9. Multiple Sequence Alignment with the Clustal series of programs Nucleic Acids Res (2003) 31 (13): 3497-500.
10. Bowie, J. U et al., (1990). Decipeing the message in Protein Sequences: Tolerance to Amino Acid Substitutions. Science 247, 1306-1310.
11. Harbour and Lane 1998. Antibodies: A Laboratory Manual, Cold Spring Harbour Press New York.[27]
12. Kohler and Milstein 1975. continuous Cultures of Fused Cells Secreting Antibody of Predefined Specficity. Nature, 256, 495-497.
13. Verhoeyen M. C Milstein, and G Winter Reshaping human antibodies: grafting an antilysozyme activity. Science 1988 Mar. 25; 239(4847):1534-6.
14. Jones, P. T., Dear, P. H., Foote, J., Neuberger, M. S. and Winter, G. *"Replacing the complementarity-determining regions in a human antibody with those from a mouse."* Nature (1986) 321: 522-525.
15. Riechmann L, Clark M, Waldmann H, Winter G. Reshaping human antibodies for therapy. Nature. 1988 Mar. 24; 332(6162):323-7.
16. Hoogenboom H R, Winter G (1992) Human antibodies from synthetic repertoires of germline VH gene segments rearranged in vitro. J Mol. Biol. 1992 Sep. 20; 227 (2):381-8.

17. Michael Neuberger (1996) Generating high-avidity human Mabs in mice *Nature Biotechnology* 14, 826
18. Tristan J. Vaughan, Jane K. Osbourn & Philip R. Tempest (1998) Human antibodies by design. Nature Biotechnology 16, 535-539
19. Milstein and Cuello (1983) The co-expression of two immunoglobulin heavy-chain/light-chain pairs, where the two heavy chains have different specificities, Nature, 305: 537-539.
20. Suresh, M. R., Cuello, A. C. and Milstein, C. (1986) Bi-specific monoclonal antibodies from hybrid hybridomas. Methods in Enzymology, 121: 210-228.
21. Brennan et al., "Preparation of bispecific antibodies by chemical recombination of monoclonal immunoglobulin G1 fragments" Science 229:81-83 (1985).
22. Hunt P J, Richards A M, Nicholls M G, Yandle T G, Doughty R N, Espiner E A. Immunoreactive amino terminal pro brain natriuretic peptide (NT-proBNP): a new marker of cardiac impairment. Clin. Endocrinol. 1997 47:287-296.
23. The Immunoassay Handbook. 3$^{rd}$ edition, ed. David Wild. Elsevier Ltd, 2005.
24. Solber H. Approved recommendation (1987) on the theory of reference values. Part 5. Statistical treatment of collected reference values. Determination of reference limits Journal of clinical Chemistry and Clinical Biochemistry 1987 25:645-656.
25. Braud V M, Allan D S, O'Callaghan C A, Soderstrom K, D'Andrea A, Ogg G S, Lazetic S, Young N T, Bell J I, Phillips J H, Lanier L L, McMichael A J. HLA-E binds to natural killer cell receptors CD94/NKG2A, B and C. Nature 1998 391:795-799.

All references and citations in this list and throughout the specification including patent specifications are hereby incorporated in their entirety.

We claim:

1. An isolated anti-BNP-SP fragment antibody or antigen-binding antibody fragment that selectively binds BNP-SP (17-26) peptide (SEQ ID NO:19).

2. An antibody or antibody fragment according to claim 1 that is labeled with a detectable marker.

3. A hybridoma that produces a monoclonal antibody that selectively binds BNP-SP (17-26) peptide (SEQ ID NO:19).

4. A recombinant cell line that produces an anti-BNP-SP fragment antibody or antigen-binding antibody fragment according to claim 1.

5. An immunoassay for determining the level of a BNP-SP (17-26) (SEQ ID NO:19) in a biological fluid sample comprising an anti-BNP-SP (17-26) (SEQ ID NO:19) fragment antibody or an anti-BNP-SP (17-26) (SEQ ID NO:19) fragment antibody fragment and a solid phase.

6. An immunoassay for determining the level of a BNP-SP (17-26) (SEQ ID NO:19) fragment in a biological fluid sample comprising an antibody or an antibody fragment that selectively binds BNP-SP (17-26) (SEQ ID NO:19), wherein the immunoassay is a competitive binding assay, a non-competitive assay, a sandwich assay, a fluoroimmunoassay, an immunofluorometric assay, an immunoradiometric assay, a luminescence assay or a chemiluniescence assay.

7. An immunoassay according to claim 5, wherein the immunoassay is a sandwich immunoassay.

8. An immunoassay according to claim 5, wherein the immunoassay is an RIA.

9. An immunoassay according to claim 5, wherein the assay is a device for sample analysis that comprises a disposable testing cartridge.

10. A method of manufacturing an acute cardiac disorder immunoassay, comprising bringing together an anti-BNP-SP fragment antibody or antibody fragment together with instructions for use in the prognosis, diagnosis, or monitoring of said acute cardiac disorder, wherein the anti-BNP-SP fragment antibody or antibody fragment selectively binds BNP-SP (17-26) peptide (SEQ ID NO:19).

11. A method of manufacture according to claim 10, wherein the immunoassay is a competitive binding assay, a non-competitive assay, a sandwich assay, a fluoroimmunoassay, an immunofluorometric assay, an immunoradiometric assay, a luminescence assay or a chemiluniescence assay.

12. A method of manufacture according to claim 10, wherein the acute cardiac disorder is unstable angina, acute myocardial infarction with ST-elevation on presenting ECG, and/or non-ST elevated myocardial infarction.

13. A kit comprising an anti-BNP-SP fragment binding agent, optionally an anti-BNP-SP fragment antibody or antigen-binding antibody fragment according to claim 1, and instructions for use in predicting, diagnosing, or monitoring an acute cardiac disorder.

14. A kit according to claim 13, wherein the anti-BNP-SP fragment binding agent is a monoclonal antibody.

15. A kit according to claim 13, wherein the kit contains an antigen-binding antibody fragment against BNP-SP (17-26) peptide (SEQ ID NO:19).

16. A kit according to claim 13, comprising an immunoassay calibrated to measure BNP-SP levels in the range of 0.1 to 500 pmol/L, 1 to 400 pmol/L, 10 to 350 pmol/L, 20 to 300 pmol/L, 25 to 250 pmol/L, 30 to 180 pmol/L, 35 to 150 pmol/L, or 40 to 120 pmol/L.

17. A kit according to claim 13 that further comprises a solid phase to which the binding agent is attached.

18. A kit according to claim 13, which includes a device for sample analysis comprising a disposable testing cartridge.

19. A kit according to claim 13, wherein the acute cardiac disorder is unstable angina, acute myocardial infarction with ST-elevation on presenting ECG, and/or non-ST elevated myocardial infarction.

20. A kit according to claim 13, wherein the kit contains an antibody against BNP-SP (17-26) peptide (SEQ ID NO:19).

21. An immunoassay according to claim 6, wherein the biological fluid specimen is from a subject having or suspected of having an acute cardiac disorder.

22. An immunoassay according to claim 21, wherein the acute cardiac disorder is unstable angina, acute myocardial infarction with ST-elevation on presenting ECG, and/or non-ST elevated myocardial infarction.

* * * * *

SEQUENCE LISTING

```
<160> NUMBER OF SEQ ID NOS: 31

<210> SEQ ID NO 1
<211> LENGTH: 134
<212> TYPE: PRT
<213> ORGANISM: Homo sapiens

<400> SEQUENCE: 1

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130

<210> SEQ ID NO 2
<211> LENGTH: 708
<212> TYPE: DNA
<213> ORGANISM: Homo sapiens

<400> SEQUENCE: 2
ccccgcaggc tgagggcagg tgggaagcaa acccggacgc atcgcagcag cagcagcagc      60
agcagaagca gcagcagcag cctccgcagt ccctccagag acatggatcc ccagacagca     120
ccttcccggg cgctcctgct cctgctcttc ttgcatctgg ctttcctggg aggtcgttcc     180
cacccgctgg gcagcccgg ttcagcctcg gacttggaaa cgtccgggtt acaggagcag     240
cgcaaccatt tgcaggcaa actgtcggag ctgcaggtgg agcagacatc cctggagccc     300
ctccaggaga gccccgtcc cacaggtgtc tggaagtccc gggaggtagc caccgagggc     360
```

-continued

| | |
|---|---|
| atccgtgggc accgcaaaat ggtcctctac accctgcggg caccacgaag ccccaagatg | 420 |
| gtgcaagggt ctggctgctt tgggaggaag atggaccgga tcagctcctc cagtggcctg | 480 |
| ggctgcaaag tgctgaggcg gcattaagag gaagtcctgg ctgcagacac ctgcttctga | 540 |
| ttccacaagg ggcttttcc tcaaccctgt ggccgccttt gaagtgactc atttttttaa | 600 |
| tgtatttatg tatttatttg attgttttat ataagatggt ttcttacctt tgagcacaaa | 660 |
| atttccacgg tgaaataaag tcaacattat aagcttttaaa aaaaaaaa | 708 |

<210> SEQ ID NO 3
<211> LENGTH: 121
<212> TYPE: PRT
<213> ORGANISM: Rattus norvegicus

<400> SEQUENCE: 3

Met Asp Leu Gln Lys Val Leu Pro Gln Met Ile Leu Leu Leu Phe
1               5                   10                  15

Leu Asn Leu Ser Pro Leu Gly Gly His Ser His Pro Leu Gly Ser Pro
            20                  25                  30

Ser Gln Ser Pro Glu Gln Ser Thr Met Gln Lys Leu Leu Glu Leu Ile
        35                  40                  45

Arg Glu Lys Ser Glu Glu Met Ala Gln Arg Gln Leu Ser Lys Asp Gln
    50                  55                  60

Gly Pro Thr Lys Glu Leu Leu Lys Arg Val Leu Arg Ser Gln Asp Ser
65                  70                  75                  80

Ala Phe Arg Ile Gln Glu Arg Leu Arg Asn Ser Lys Met Ala His Ser
                85                  90                  95

Ser Ser Cys Phe Gly Gln Lys Ile Asp Arg Ile Gly Ala Val Ser Arg
            100                 105                 110

Leu Gly Cys Asp Gly Leu Arg Leu Phe
        115                 120

<210> SEQ ID NO 4
<211> LENGTH: 628
<212> TYPE: DNA
<213> ORGANISM: Rattus norvegicus

<400> SEQUENCE: 4

| | |
|---|---|
| gcgagacaag agagagcagg acaccatcgc agctgcctgg cccatcactt ctgcagcatg | 60 |
| gatctccaga aggtgctgcc ccagatgatt ctgctcctgc ttttccttaa tctgtcgccg | 120 |
| ctgggaggtc actcccatcc cctgggaagt cctagccagt ctccagaaca atccacgatg | 180 |
| cagaagctgc tggagctgat aagagaaaag tcagaggaaa tggctcagag acagctctca | 240 |
| aaggaccaag ccctacaaa agaacttcta aaaagagtcc ttaggtctca agacagcgcc | 300 |
| ttccggatcc aggagagact cgaaattcc aagatggcac atagttcaag ctgctttggg | 360 |
| cagaagatag accggatcgg cgcagtcagt cgcttgggct gtgacgggct gaggttgttt | 420 |
| taggaagacc tcctggctgc agactccggc ttctgactct gcctgcggct cttctttccc | 480 |
| cagctctggg accacctctc aagtgatcct gtttatttat ttgtttattt atttattttt | 540 |
| atgttgctga ttttctacaa gactgttct tatcttccag cacaaacttg ccacagtgta | 600 |
| ataaacatag cctatttctt gcttttgg | 628 |

<210> SEQ ID NO 5
<211> LENGTH: 129
<212> TYPE: PRT
<213> ORGANISM: Ovis aries

<400> SEQUENCE: 5

```
Met Asp Pro Gln Lys Ala Leu Ser Arg Thr Leu Leu Leu Leu Phe
1               5                  10                  15

Leu His Leu Ser Leu Leu Gly Cys Arg Ser His Pro Leu Gly Gly Pro
            20                  25                  30

Gly Ser Ala Ser Glu Leu Pro Gly Leu Gln Glu Leu Leu Asp Arg Leu
        35                  40                  45

Arg Asp Arg Val Ser Glu Leu Gln Ala Glu Gln Leu Arg Val Glu Pro
    50                  55                  60

Leu Gln Gln Gly Gln Gly Leu Glu Glu Thr Trp Asp Ser Pro Ala Ala
65                  70                  75                  80

Ala Pro Ala Gly Phe Leu Gly Pro His His Ser Leu Leu Gln Ala Leu
                85                  90                  95

Arg Gly Pro Lys Met Met Arg Asp Ser Gly Cys Phe Gly Arg Arg Leu
            100                 105                 110

Asp Arg Ile Gly Ser Leu Ser Gly Leu Gly Cys Asn Val Leu Arg Arg
        115                 120                 125

Tyr
```

<210> SEQ ID NO 6
<211> LENGTH: 2125
<212> TYPE: DNA
<213> ORGANISM: Ovis aries

<400> SEQUENCE: 6

```
gcttgtcttt ctggcaacac cggagttgag gagagcaaga actcttgcgt tggtggctca      60
gcgtgatcag aaccacggac agcggtcagc gcgcccgagg gaccggcggt ctggcgcagg     120
gcagagttgc aggcttgcgc tcttccaggc ggggtgccga gttccaggcg gggagggaag     180
acgcgctgca gtgatggggt gttggctggg ctgttctttg tgagtcacc tcgtgcgccc     240
ggcatttgcg tcgagtctct gatcgctggg gttctctctt ctcaattcag gaatgggggt     300
ggggaggaaa gaaaaaaatc cacgctaatg ccccggcgg ttttgcagga aggaagcag      360
agagagagac gaaaggctat tggtgtctac ccctccctgc ctacgccccc actcccgcac     420
cccaccctc caaaccccc cgcccccac cccgggcgcg cgttccagct cccggtcagg       480
cccatttcta tacaaggcct gctctccca gctccaccc ctcggcgcg gagaggtgca       540
ttccccgcc ctgagctcag cgggtcgggc cggaatgcgg ccgataaatc agagataacc     600
cagagaggca gggccggccc agctcccagg accagggata aaaggcctct gttgcccaag     660
gatccgggag agcgcccacc gggcactaga aggtgagacg tgaggcgcaa cccagcgaag     720
cagccgcggc cgcaacccag gaccagggat aaaaggcctc tgttgcccaa ggatccggga     780
gagcgcccac cgggcactag aaggtgagac gtgaggcgca acccagcgaa gcagccgcgg     840
ccgcaacctc catccgctcc gccagcgaca tggaccccca gaaggcgctg tcccgaacgc     900
tcctgcttct cctcttcttg cacctgtcgc tgctaggatg tcgttcccac ccgctgggtg     960
gccccggctc ggcttcggaa ctgcctgggt tacaggtgag cgctgctgaa ctgcgtaaac    1020
ccggttcgcc aagagggcgc ggacagcagc agttagcggg tccccatccc ccgaccctcc    1080
actcacatcc caagaggtcc ccaccctccc ttgggaatta gtgataccag aatcagaaag    1140
ggaattagaa catggagaga ctgggtgcgg gaagccggta cccagcgcgg ttggatcgct    1200
ttgccgccgt cgagggtggc tgggcccaag gtgcgggttt ctgaagatgc ggctcccta     1260
ccgtgcattg caggagctgt tggaccgtct acgagacagg gtctcggagc tgcaggcgga    1320
```

-continued

```
gcagctgcgc gtggagcccc tccagcaggg ccagggcctg gaagaaacct gggactcccc    1380
ggcggcagcc cccgcggggt tccttgggcc ccaccacagc ctcctccagg ccctgcgggg    1440
ccccaagatg atgcgcgact cgggctgctt tggacggagg ctggaccgga tcggctccct    1500
cagtggcctg ggctgcaacg gtgagcgcct atccgcattc ccactgcaca tcaccattag    1560
agccacttct gggtccgatg tctcagggga ccaaattttg aacaagaac atcactcttc    1620 tttgctggca gtcctcaggg ccaaggcatg cctctctggg aatattaaat ttggacaaca    1680
ttcattatca tgtctgggag cccttctat ccacctcctg cctctgactg aaaggggcag     1740
aatctttagg atgtaattca gtcactgttc agcaggccct ccttggagca aaagaatag     1800 ttaacatttt tcctcctggt ttcccctgaa ctgtctaaag ctgcaaaggc agaggggggg    1860
gtcaccaggg ggatggtaat ccctggttta caaggaggat ggggaggtcc ggggagatgg    1920
gttattccaa agccccaaac atgcagatga actgaagagg ggggtggcag ggtggcaca     1980 gggtgaggga aagctcagat ccttcctgtc tcccacccca aagtcatcat caccctctct    2040 tttccccca cagtgctgag gaggtactaa gaggaggtcc tggctgcaga tatggctgca    2100
tctgattctc catcaactcc tgatc                                           2125
```

<210> SEQ ID NO 7
<211> LENGTH: 131
<212> TYPE: PRT
<213> ORGANISM: Sus scrofa

<400> SEQUENCE: 7

Met Gly Pro Arg Met Ala Leu Pro Arg Val Leu Leu Leu Phe Leu
1               5                   10                  15

His Leu Leu Leu Gly Cys Arg Ser Tyr Pro Leu Gly Gly Ala Gly
                20                  25                  30

Leu Ala Ser Glu Leu Pro Gly Ile Gln Glu Leu Leu Asp Arg Leu Arg
            35                  40                  45

Asp Arg Val Ser Glu Leu Gln Ala Glu Arg Thr Asp Leu Glu Pro Leu
    50                  55                  60

Arg Gln Asp Arg Gly Leu Thr Glu Ala Trp Glu Ala Arg Glu Ala Ala
65                  70                  75                  80

Pro Thr Gly Val Leu Gly Pro Arg Ser Ser Ile Phe Gln Val Leu Arg
                85                  90                  95

Gly Ile Arg Ser Pro Lys Thr Met Arg Asp Ser Gly Cys Phe Gly Arg
            100                 105                 110

Arg Leu Asp Arg Ile Gly Ser Leu Ser Gly Leu Gly Cys Asn Val Leu
        115                 120                 125

Arg Arg Tyr
    130

<210> SEQ ID NO 8
<211> LENGTH: 670
<212> TYPE: DNA
<213> ORGANISM: Sus scrofa

<400> SEQUENCE: 8

```
caggctgcta ggaagtgaaa agtgaacctg acccagctc agcggcagca gcagcggcag      60
caggcagcag cctctatcct ctcctccagc cacatgggcc ccggatggc gcttcccgc      120 gtgctcctgc tcctgttctt gcacctgttg ctgctaggat gccgttccta tccactgggt    180
ggcgctggcc tggcctcaga actgccaggg atacaggagc tgctggaccg cctgcgagac    240
```

```
agggtctccg agctgcaggc ggagcggacg gacctggagc ccctccggca ggaccgtggc    300
ctcacagaag cctgggaggc gagggaagca gcccccacgg gggttcttgg gccccgcagt    360
agcatcttcc aagtcctccg gggaatacgc agccccaaga cgatgcgtga ctctggctgc    420
tttgggcgga ggctggaccg gatcggctcc ctcagcggcc tgggctgcaa tgtgctcagg    480
aggtactgag aagtcctggc tgacaacctc tgtgtccgct tctccaacgc ccctcccctg    540
ctccccttca aagcaactcc tgttttttatt tatgtattta tttattttatt tatttggtgg    600 ttgtatataa gacggttctt atttgtgagc acattttttc catggtgaaa taaagtcaac    660
attagagctc                                                          670
```

```
<210> SEQ ID NO 9
<211> LENGTH: 121
<212> TYPE: PRT
<213> ORGANISM: Mus musculus

<400> SEQUENCE: 9

Met Asp Leu Leu Lys Val Leu Ser Gln Met Ile Leu Phe Leu Leu Phe
  1               5                  10                  15

Leu Tyr Leu Ser Pro Leu Gly Gly His Ser Tyr Pro Leu Gly Ser Pro
             20                  25                  30

Ser Gln Ser Pro Glu Gln Phe Lys Met Gln Lys Leu Leu Glu Leu Ile
         35                  40                  45

Arg Glu Lys Ser Glu Glu Met Ala Gln Arg Gln Leu Leu Lys Asp Gln
     50                  55                  60

Gly Leu Thr Lys Glu His Pro Lys Arg Val Leu Arg Ser Gln Gly Ser
 65                  70                  75                  80

Thr Leu Arg Val Gln Gln Arg Pro Gln Asn Ser Lys Val Thr His Ile
                 85                  90                  95

Ser Ser Cys Phe Gly His Lys Ile Asp Arg Ile Gly Ser Val Ser Arg
            100                 105                 110

Leu Gly Cys Asn Ala Leu Lys Leu Leu
        115                 120
```

```
<210> SEQ ID NO 10
<211> LENGTH: 667
<212> TYPE: DNA
<213> ORGANISM: Mus musculus

<400> SEQUENCE: 10
cgaccaccag tgcacaagct gcttggggag gcgagacaag ggagaacacg gcatcattgc     60
ctggcccatc gcttctgcgg catggatctc ctgaaggtgc tgtcccagat gattctgttt    120
ctgcttttcc tttatctgtc accgctggga ggtcactcct atcctctggg aagtcctagc    180
cagtctccag agcaattcaa gatgcagaag ctgctggagc tgataagaga aaagtcggag    240
gaaatggccc agagacagct cttgaaggac caaggcctca caaaagaaca cccaaaaaga    300
gtccttcggt ctcaaggcag caccctccgg gtccagcaga gacctcaaaa ttccaaggtg    360
acacatatct caagctgctt tgggcacaag atagaccgga tcggatccgt cagtcgtttg    420
ggctgtaacg cactgaagtt gttgtaggaa gacctcctgg ctgcaggaga ctccagtttc    480
tgactctgcc tgggtctctt tccccagctc tgggaccacc tttgaagtga tcctatttat    540
ttatttattt atatttattt ttatttttat ttttaatttt attttgttgt ttttctacaa    600
gactgtttct tatcttggag cacaaacttg ccacaacata taaacatag cgtatttcct    660 gcttttg                                                             667
```

```
<210> SEQ ID NO 11
<211> LENGTH: 140
<212> TYPE: PRT
<213> ORGANISM: Canis familiaris

<400> SEQUENCE: 11

Met Glu Pro Cys Ala Ala Leu Pro Arg Ala Leu Leu Leu Leu Leu Phe
1               5                   10                  15

Leu His Leu Ser Pro Leu Gly Gly Arg Pro His Pro Leu Gly Gly Arg
            20                  25                  30

Ser Pro Ala Ser Glu Ala Ser Glu Ala Ser Glu Ala Ser Gly Leu Trp
        35                  40                  45

Ala Val Gln Glu Leu Leu Gly Arg Leu Lys Asp Ala Val Ser Glu Leu
    50                  55                  60

Gln Ala Glu Gln Leu Ala Leu Glu Pro Leu His Arg Ser His Ser Pro
65                  70                  75                  80

Ala Glu Ala Pro Glu Ala Gly Gly Thr Pro Arg Gly Val Leu Ala Pro
                85                  90                  95

His Asp Ser Val Leu Gln Ala Leu Arg Arg Leu Arg Ser Pro Lys Met
            100                 105                 110

Met His Lys Ser Gly Cys Phe Gly Arg Arg Leu Asp Arg Ile Gly Ser
        115                 120                 125

Leu Ser Gly Leu Gly Cys Asn Val Leu Arg Lys Tyr
    130                 135                 140

<210> SEQ ID NO 12
<211> LENGTH: 132
<212> TYPE: PRT
<213> ORGANISM: Felis catus

<400> SEQUENCE: 12

Met Asp Pro Lys Thr Ala Leu Arg Ala Leu Leu Leu Leu Leu Leu Phe
1               5                   10                  15

Leu His Leu Ser Pro Leu Gly Gly Arg Ser His Pro Leu Gly Gly Pro
            20                  25                  30

Gly Pro Ala Ser Glu Ala Ser Ala Ile Gln Glu Leu Leu Asp Gly Leu
        35                  40                  45

Arg Asp Thr Val Ser Glu Leu Gln Glu Ala Gln Met Ala Leu Gly Pro
    50                  55                  60

Leu Gln Gln Gly His Ser Pro Ala Glu Ser Trp Glu Ala Gln Glu Glu
65                  70                  75                  80

Pro Pro Ala Arg Val Leu Ala Pro His Asp Asn Val Leu Arg Ala Leu
                85                  90                  95

Arg Arg Leu Gly Ser Ser Lys Met Met Arg Asp Ser Arg Cys Phe Gly
            100                 105                 110

Arg Arg Leu Asp Arg Ile Gly Ser Leu Ser Gly Leu Gly Cys Asn Val
        115                 120                 125

Leu Arg Arg His
    130

<210> SEQ ID NO 13
<211> LENGTH: 10
<212> TYPE: PRT
<213> ORGANISM: Homo sapiens

<400> SEQUENCE: 13

Met Asp Pro Gln Thr Ala Pro Ser Arg Ala
1               5                   10
```

<210> SEQ ID NO 14
<211> LENGTH: 30
<212> TYPE: DNA
<213> ORGANISM: Homo sapiens

<400> SEQUENCE: 14
ccccgcaggc tgagggcagg tgggaagcaa                              30

<210> SEQ ID NO 15
<211> LENGTH: 17
<212> TYPE: PRT
<213> ORGANISM: Homo sapiens

<400> SEQUENCE: 15

Met Asp Pro Gln Thr Ala Pro Ser Arg Ala Leu Leu Leu Leu Leu Phe
1               5                   10                  15

Leu

<210> SEQ ID NO 16
<211> LENGTH: 51
<212> TYPE: DNA
<213> ORGANISM: Homo sapiens

<400> SEQUENCE: 16
ccccgcaggc tgagggcagg tgggaagcaa acccggacgc atcgcagcag c        51

<210> SEQ ID NO 17
<211> LENGTH: 12
<212> TYPE: PRT
<213> ORGANISM: Homo sapiens

<400> SEQUENCE: 17

Leu Leu Leu Leu Phe Leu His Leu Ala Phe Leu Gly
1               5                   10

<210> SEQ ID NO 18
<211> LENGTH: 36
<212> TYPE: DNA
<213> ORGANISM: Homo sapiens

<400> SEQUENCE: 18
cggacgcatc gcagcagcag cagcagcagc agaagc                       36

<210> SEQ ID NO 19
<211> LENGTH: 10
<212> TYPE: PRT
<213> ORGANISM: Homo sapiens

<400> SEQUENCE: 19

Leu His Leu Ala Phe Leu Gly Gly Arg Ser
1               5                   10

<210> SEQ ID NO 20
<211> LENGTH: 30
<212> TYPE: DNA
<213> ORGANISM: Homo sapiens

<400> SEQUENCE: 20
agcagcagca gcagcagaag cagcagcagc                              30

<210> SEQ ID NO 21
<211> LENGTH: 26
<212> TYPE: PRT
<213> ORGANISM: Homo sapiens

```
<400> SEQUENCE: 21

Met Asp Pro Gln Thr Ala Pro Ser Arg Ala Leu Leu Leu Leu Phe
1               5                   10                  15

Leu His Leu Ala Phe Leu Gly Gly Arg Ser
            20                  25

<210> SEQ ID NO 22
<211> LENGTH: 78
<212> TYPE: DNA
<213> ORGANISM: Homo sapiens

<400> SEQUENCE: 22
ccccgcaggc tgagggcagg tgggaagcaa acccggacgc atcgcagcag cagcagcagc    60
agcagaagca gcagcagc                                                  78

<210> SEQ ID NO 23
<211> LENGTH: 13
<212> TYPE: PRT
<213> ORGANISM: Homo sapiens

<400> SEQUENCE: 23

Pro Gln Thr Ala Pro Ser Arg Ala Leu Leu Leu Leu Leu
1               5                   10

<210> SEQ ID NO 24
<211> LENGTH: 39
<212> TYPE: DNA
<213> ORGANISM: Homo sapiens

<400> SEQUENCE: 24
aggctgaggg caggtgggaa gcaaacccgg acgcatcgc                           39

<210> SEQ ID NO 25
<211> LENGTH: 30
<212> TYPE: DNA
<213> ORGANISM: Homo sapiens

<400> SEQUENCE: 25
ccagtgcaca agctgcttgg ggaggcgaga                                     30

<210> SEQ ID NO 26
<211> LENGTH: 26
<212> TYPE: PRT
<213> ORGANISM: Felis catus

<400> SEQUENCE: 26

Met Asp Pro Lys Thr Ala Leu Leu Arg Ala Leu Leu Leu Leu Phe
1               5                   10                  15

Leu His Leu Ser Pro Leu Gly Gly Arg Ser
            20                  25

<210> SEQ ID NO 27
<211> LENGTH: 26
<212> TYPE: PRT
<213> ORGANISM: Ovis aries

<400> SEQUENCE: 27

Met Asp Pro Gln Lys Ala Leu Ser Arg Thr Leu Leu Leu Leu Phe
1               5                   10                  15

Leu His Leu Ser Leu Leu Gly Cys Arg Ser
            20                  25
```

-continued

```
<210> SEQ ID NO 28
<211> LENGTH: 25
<212> TYPE: PRT
<213> ORGANISM: Sus scrofa

<400> SEQUENCE: 28

Met Gly Pro Arg Met Ala Leu Pro Arg Val Leu Leu Leu Leu Phe Leu
1               5                   10                  15

His Leu Leu Leu Leu Gly Cys Arg Ser
            20                  25

<210> SEQ ID NO 29
<211> LENGTH: 26
<212> TYPE: PRT
<213> ORGANISM: Canis familiaris

<400> SEQUENCE: 29

Met Glu Pro Cys Ala Ala Leu Pro Arg Ala Leu Leu Leu Leu Leu Phe
1               5                   10                  15

Leu His Leu Ser Pro Leu Gly Gly Arg Pro
            20                  25

<210> SEQ ID NO 30
<211> LENGTH: 26
<212> TYPE: PRT
<213> ORGANISM: Rattus norvegicus

<400> SEQUENCE: 30

Met Asp Leu Gln Lys Val Leu Pro Gln Met Ile Leu Leu Leu Leu Phe
1               5                   10                  15

Leu Asn Leu Ser Pro Leu Gly Gly His Ser
            20                  25

<210> SEQ ID NO 31
<211> LENGTH: 26
<212> TYPE: PRT
<213> ORGANISM: Mus musculus

<400> SEQUENCE: 31

Met Asp Leu Leu Lys Val Leu Ser Gln Met Ile Leu Phe Leu Leu Phe
1               5                   10                  15

Leu Tyr Leu Ser Pro Leu Gly Gly His Ser
            20                  25
```